United States Patent [19]

Gray et al.

[11] Patent Number: 5,229,413
[45] Date of Patent: Jul. 20, 1993

[54] COMPOSITIONS CONTAINING INDOLE-2-CARBOXYLATE COMPOUNDS FOR TREATMENT OF CNS DISORDERS

[75] Inventors: Nancy M. Gray, Ellisville; Brian K. Cheng, St. Charles; William F. Hood, St. Louis; Michael S. Dappen, Chesterfield; Alex A. Cordi, St. Louis, all of Mo.

[73] Assignee: G. D. Searle & Co., Chicago, Ill.

[21] Appl. No.: 830,108

[22] Filed: Feb. 3, 1992

Related U.S. Application Data

[63] Continuation of Ser. No. 484,530, Mar. 1, 1990, Pat. No. 5,137,910, which is a continuation-in-part of Ser. No. 348,333, May 5, 1989, abandoned.

[51] Int. Cl.$^5$ .................. A61K 31/40; A61K 31/405; C07D 209/18; C07D 209/42
[52] U.S. Cl. .................... 514/415; 514/419; 514/423; 548/469; 548/492; 548/493; 548/494; 548/503; 548/504; 548/509
[58] Field of Search ........ 514/415, 419, 423; 548/464, 492, 493, 494, 503, 504, 509

[56] References Cited

U.S. PATENT DOCUMENTS

| | | | |
|---|---|---|---|
| 3,072,530 | 1/1963 | Hoffman et al. | 514/415 |
| 3,078,214 | 2/1963 | Hoffman et al. | 514/415 |
| 3,296,072 | 1/1967 | Szmusz Kovicz | 514/415 |
| 3,531,573 | 9/1970 | Anthony | 514/415 |
| 3,720,771 | 3/1973 | Canas-Rodriquez et al. | 514/415 |
| 4,022,778 | 5/1977 | Freed | 548/492 |
| 4,672,074 | 6/1987 | Harendza-Harinxma | 514/420 |
| 4,847,283 | 7/1989 | Harendza-Harinxma | 514/415 |

FOREIGN PATENT DOCUMENTS

| | | |
|---|---|---|
| 352708 | 10/1979 | Austria . |
| 0034270 | 10/1965 | France . |
| 7331854 | 9/1973 | France . |
| 44-8502 | 4/1969 | Japan . |
| 46-39098 | 11/1971 | Japan . |
| 47-37166 | 9/1972 | Japan . |
| 63-198622 | 8/1988 | Japan . |
| 69-02641 | 1/1971 | Netherlands . |
| 195444 | 2/1951 | Spain . |
| 1153954 | 8/1973 | United Kingdom . |

OTHER PUBLICATIONS

V. V. Feofilaktov et al, *Zhur. Obshchei Khim.*, 23, 644–656 (1953).
L. Kalb et al, *Chem. Ber.*, 59B, 1860–1870 (1926).
R. W. Jackson et al, *J. Am. Chem. Soc.*, 52, 5029–5035 (1930).
R. H. F. Manske et al, *Can. J. Chem.*, 38, 620–621 (1960).
O. L. Hoffman et al, *J. Biol. Chem.*, 196, 437–441 (1952).
I. A. Kemp et al, *Proc. Natl. Acad. Sci. USA*, 85, 6547–6550 (1988).
A. C. Foster et al, *Nature*, 338, 377–378 (1989).
M. Passerini et al, *Gazz. Chim Ital.*, 69, 658–664 (1939).
S. M. Rothman and J. W. Olney, "Glutamate and the Pathophysiology of Hypoxia–Ischemic Brain Damage," *Annals of Neurology*, vol. 19, No. 2 (1986).
J. W. Johnson et al, *Nature* (London), 325, 529–531 (1987).
G. B. Watson et al, *Neurosci. Res. Comm.*, 2, (3), 169–174 (1988).
Sumitome, Chem. Abstracts, 110:44972, (1989).

*Primary Examiner*—Nathan M. Nutter
*Attorney, Agent, or Firm*—J. Timothy Keane; Charles E. Smith; Paul D. Matukaitis

[57] ABSTRACT

Compositions containing certain indole-2-carboxylate compounds and derivatives are described as being therapeutically effective in treatment of CNS disorders resulting from neurotoxic damage or neurodegenerative diseases, particularly those CNS disorders resulting from ischemic events. Preferred compounds are of the formula

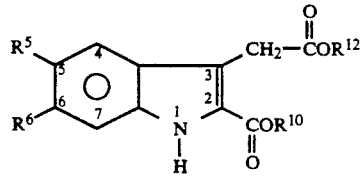

wherein each of $R^5$ and $R^6$ is independently selected from hydrido, bromo, chloro and fluoro, and wherein each of $R^{10}$ and $R^{12}$ is independently selected from hydrido and lower alkyl, and pharmaceutically-acceptable salts thereof.

8 Claims, 3 Drawing Sheets

COMPOSITIONS CONTAINING INDOLE-2-CARBOXYLATE COMPOUNDS FOR TREATMENT OF CNS DISORDERS

CROSS-REFERENCE TO RELATED APPLICATION

This is a continuation of application Ser. No. 07/484,530 filed Mar. 1, 1990, and now U.S. Pat. No. 5,132,910 which application is a continuation-in-part application of U.S. application Ser. No. 07/348,333 filed May 5, 1989 and now abandoned.

FIELD OF THE INVENTION

This invention is in the field of clinical neurology and relates specifically to a class of therapeutically useful compounds, compositions and methods for management of neurotoxic damage or neurodegenerative diseases. For example, these compounds are particularly useful for treating neurotoxic injury which follows periods of hypoxia, anoxia or ischemia associated with stroke, cardiac arrest or perinatal asphyxia. The compounds would also be useful as anti-convulsants and for treatment of epilepsy.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia—Ischemic Brain Damage," *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with hypoxia, anoxia, or ischemia caused by stroke, cardiac arrest or perinatal asphyxia.

It is known that glycine potentiates NMDA receptor-mediated responses. Also, there has been observed an allosteric interaction of glycine through a strychnineinsensitive glycine recognition site which is believed to form part of the NMDA receptor-ion channel complex [J. W. Johnson et al, *Nature (London)*, 325, 529–531 (1987)]. For example, the compound 2-carboxy-4-hydroxyquinoline (also known as kynurenic acid) is a known NMDA antagonist and its NMDA antagonist activity can be reversed by the presence of glycine [G. B. Watson et al, *Neurosci. Res. Comm.*, 2, No. 3, 169–174 (1988)]. Also, the compound 7-chlorokynurenic acid has been shown to be an NMDA antagonist whose blocking effect can be reversed by glycine [I. A. Kemp et al, *Proc. Natl. Acad. Sci. USA*, 85 6547–6550 (1988)]. An excess of glycine may cause neuronal excitation and lead to overactivation of NMDA receptors which has been linked to seizure disorders and neurodegenerative disease [A. C. Foster et al, *Nature*, 377–378 (1989)].

Derivatives of indolecarboxylate compounds are known. For example, 2-carboxy-3-indoleacetic acid has been prepared from a hydrazone precursor [M. Passerini et al, *Gazz. Chim. Ital.*, 69, 658–664 (1939)]. Similarly, the compounds 2-carboxy-5-chloro-3-indoleacetic acid and ethyl 2-ethoxycarbonyl-3indoleacetic acid have been prepared from hydrazone precursors [V. V. Feofilaktov et al, *Zhur. Obshchei Khim.*, 23, 644–656 (1953)]. Also, the compound 2-carboxy-3-indolepropionic acid has been prepared from the hydrazone precursor [L. Kalb et al, *Chem. Ber.*, 59B, 1860–1870 (1926)]. The compounds 2-carboxy-3-indolebutyric acid and its ester, ethyl 2-carboxy-3-indolebutyrate, likewise have been prepared from hydrazone precursors [R. W. Jackson et al, *J. Am. Chem. Soc.*, 52, 5029–5035 (1930); R. H. F. Manske et al, *Can. J. Chem.*, 38, 620–621 (1960)].

Some indolecarboxylate compounds have been found to have agricultural-related utility. For example, Spanish Patent No. 195,444 describes ethyl 2-ethoxycarbonyl-3-indoleacetic acid as having phytohormonal activity. The compounds 5-bromo-2-carboxy-3-indoleacetic acid, 5-methyl-2-carboxy-3-indoleacetic acid and 7-chloro-2-carboxy-3-indoleacetic acid have been described as having auxin-like activity [O. L. Hoffmann et al, *J. Biol. Chem.*, 196, 437–441 (1952)].

Other indolecarboxylate compounds and derivatives have been found to have pharmacological activity. For example, U.K. Patent No. 1,153,954 describes N-carbonyl/sulfonyl-3-indolylacetic acids as having antiinflammatory and antipyretic activity. Netherlands Patent No. 69-02641 describes N-carboxyalkyl-3-indoleacetic acid compounds as antiinflammatory and antipyretic agents.

Certain indole-2-carboxylate compounds lacking substitution on the indole nitrogen atom are known to have pharmacological activity. For example, Japanese Patent No. 69-8502 describes indoxylcarboxylic acid compounds having an unsubstituted indole nitrogen atom as antiinflammatory agents. Austrian Patent No. 352,708 describes 2-(alkoxycarbonyl)-3-indolealkanoic acid compounds having an unsubstituted indole nitrogen atom as antipyretic agents.

DESCRIPTION OF THE INVENTION

Figure 1:
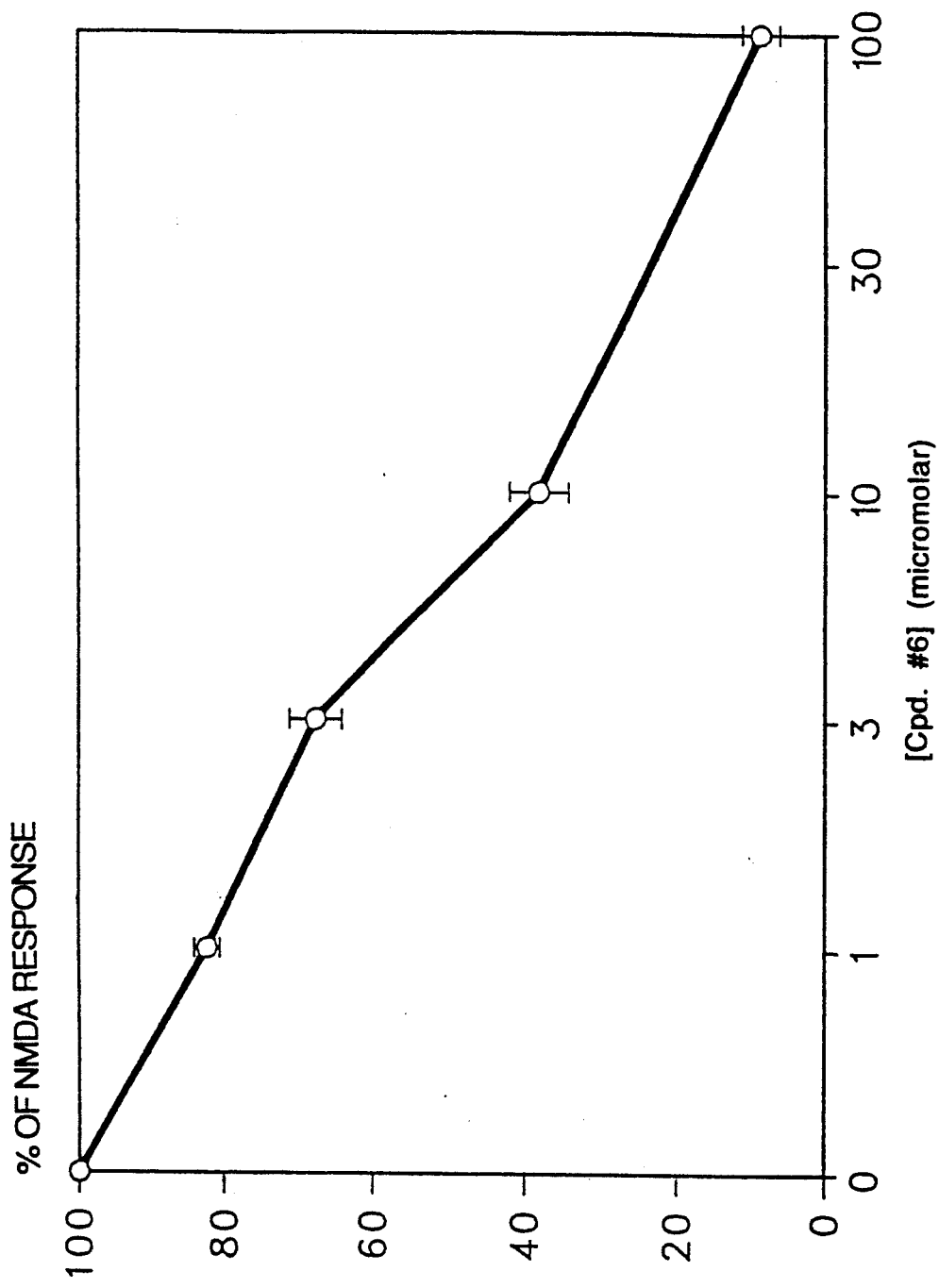
FIG. 1 is a graph showing the activity of a compound of the invention in blocking the effects of glycine stimulation in *Xenopus* oocyte.
Figure 2:
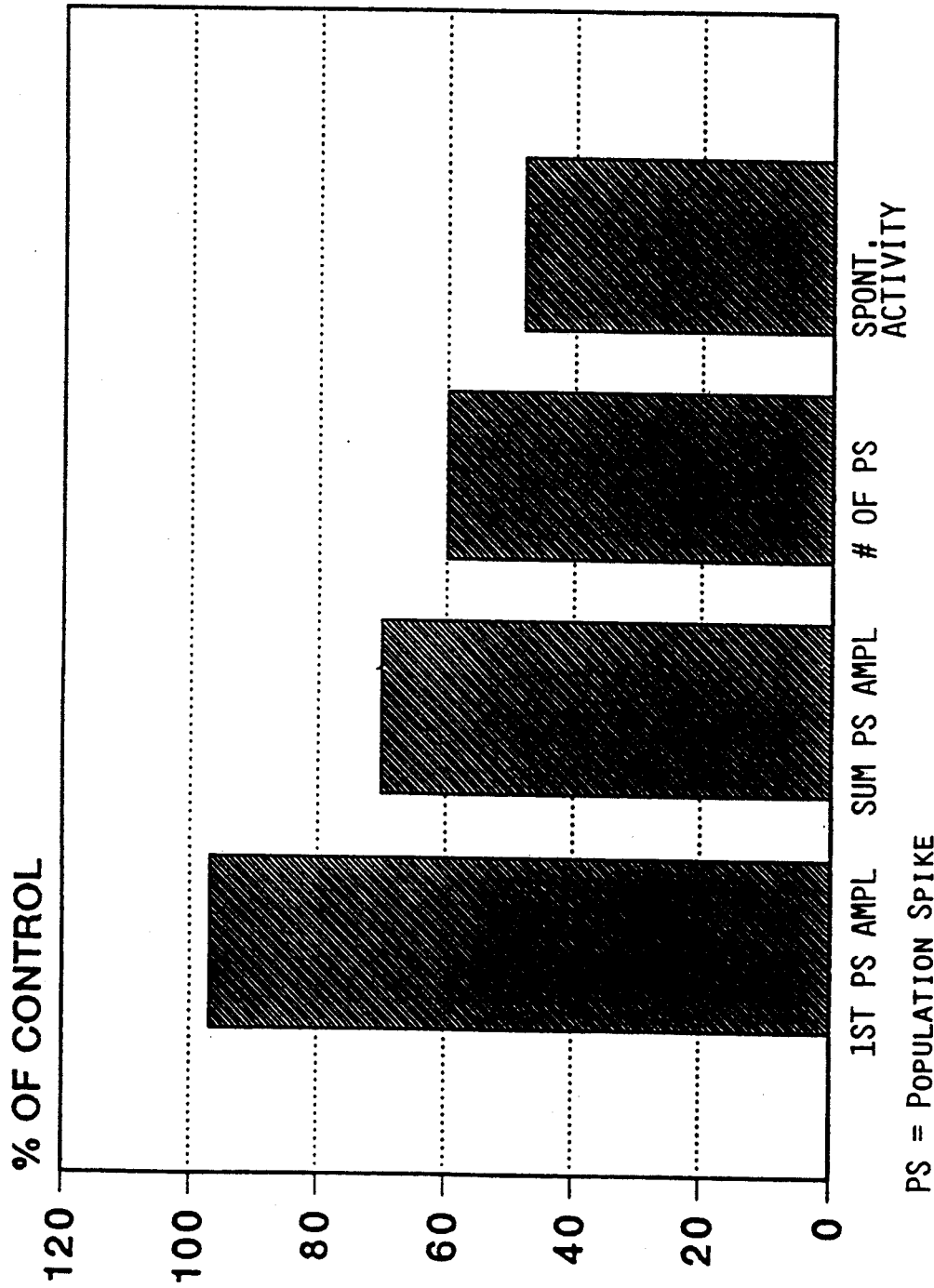
FIG. 2 is a graph showing the activity of a compound of the invention in blocking the effects of glycine stimulation in epileptic hippocampal slice.
Figure 3:
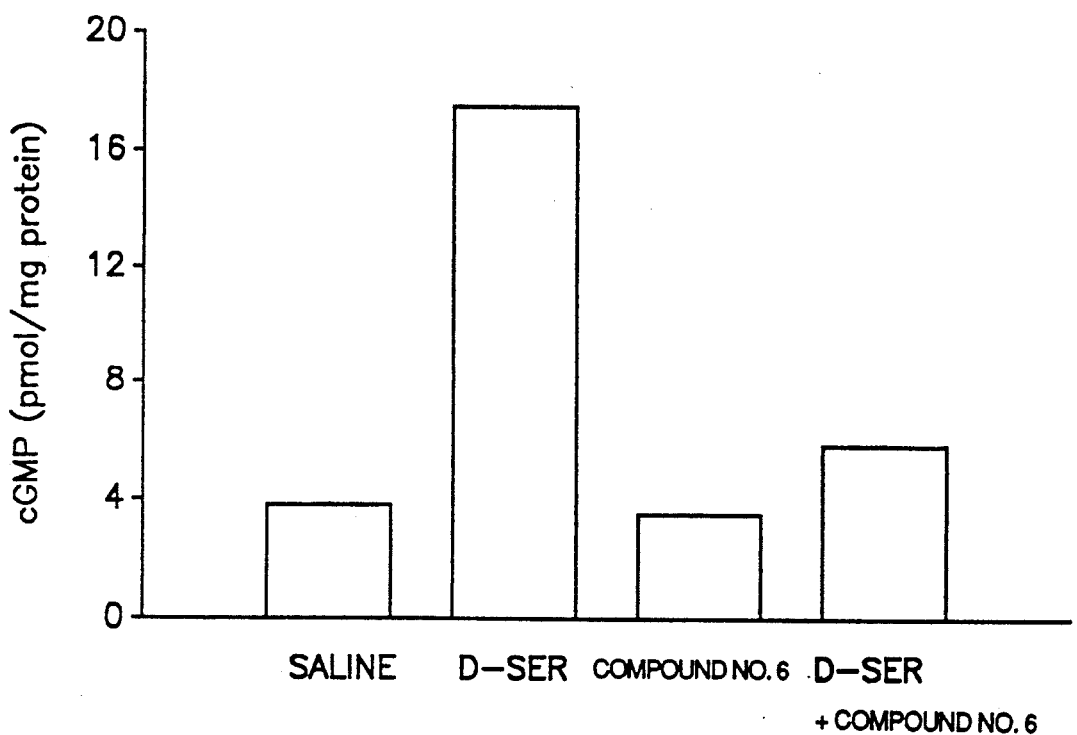
FIG. 3 is a graph showing blockage of agonist-induced effects on cGMP by a compound of the invention.

Treatment of a mammal afflicted by or susceptible to a neurodegenerative disease or neurotoxic injury is provided by administering to the mammal a therapeutically-effective amount of one or more compounds selected from a class of indole-2-carboxylate compounds and derivatives defined by Formula I:

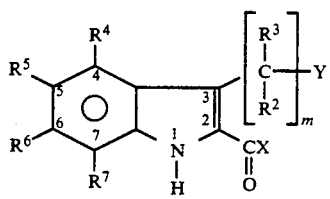

wherein $R^1$ is selected from hydrido, alkyl and aralkyl; wherein each of $R^2$ through $R^7$ is independently selected from hydrido, halo, hydroxy, alkyl, haloalkyl, alkoxy, hydroxyalkyl, cycloalkyl, cycloalkylalkyl, aralkyl, alkoxyalkyl, cyano, alkylthio, sulfinyl, sulfonyl, sulfinylalkyl, sulfonylalkyl, amino, monoalkylamino, dialkylamino, acyl, acyloxy, amido, aryloxy, aralkoxy, aralkoxyalkyl, aryl and

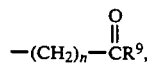

wherein $R^9$ is selected from hydrido, halo, hydroxy, alkyl, alkoxy, cycloalkyl, cycloalkylalkyl, cycloalkyloxy, aryl, aryloxy, aralkyl, aralkyloxy, amino, monoalkylamino and dialkylamino, wherein n is a whole number selected from zero through six; wherein X is selected from hydrido, halo, amino, monoalkylamino, dialkylamino and $OR^{10}$ wherein $R^{10}$ is selected from hydrido, alkyl, cycloalkyl, cycloalkylalkyl, aralkyl and aryl; wherein Y is selected from hydrido, alkyl, hydroxy, halo, cycloalkyl, alkoxy, aryl and

wherein $R^{11}$ is selected from hydrido, hydroxy, alkyl, alkoxy, cycloalkyl, cycloalkylalkyl, cycloalkyloxy, aryl, aryloxy, aralkyl, aralkyloxy, amino, monoalkylamino and dialkylamino; wherein m is a number selected from zero through six; and wherein any of the foregoing X, Y and $R^1$ through $R^{11}$ substituents having a substitutable position is substituted with a radical selected from alkyl, halo, hydroxy, alkoxy, amino, monoalkylamino, dialkylamino, monoaralkylamino, dia- ralkylamino, haloalkyl, aralkyl and aryl; or a pharmaceutically-acceptable salt or ester thereof.

A preferred class of compounds within Formula I consists of those compounds wherein $R^1$ is selected from hydrido, alkyl and aralkyl; wherein each of $R^2$ through $R^7$ is independently selected from hydrido, halo, hydroxy, alkyl, haloalkyl, alkoxy, hydroxyalkyl, cycloalkyl, cycloalkylalkyl, aralkyl, alkoxyalkyl, cyano, alkylthio, amino, monoalkylamino, dialkylamino, acyl, acyloxy, amido, aryloxy, aralkoxy, aralkoxyalkyl, aryl and

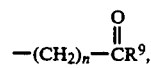

wherein $R^9$ is selected from hydrido, halo, hydroxy, alkyl, alkoxy, cycloalkyl, cycloalkylalkyl, cycloalkyloxy, aryl, aryloxy, aralkyl, aralkyloxy, amino, monoalkylamino and dialkylamino, wherein n is a number selected from zero through four; wherein X is selected from halo, amino, monoalkylamino, dialkylamino and $OR^{10}$ wherein $R^{10}$ is selected from hydrido, alkyl, cycloalkyl, cycloalkylalkyl, aralkyl and aryl; wherein Y is selected from hydroxy, halo, alkoxy and

wherein $R^{11}$ is selected from hydrido, halo, hydroxy, alkyl, alkoxy, cycloalkyl, cycloalkylalkyl, cycloalkyloxy, aryl, aryloxy, aralkyl, aralkyloxy, amino, monoalkylamino and dialkylamino; wherein m is a number selected from zero through four; and wherein any of the foregoing X Y and $R^1$ through $R^{11}$ substituents having a substitutable position is substituted with a radical selected from alkyl, hydroxy, alkoxy, amino, monoalkylamino, dialkylamino, monophenalkylamino, aralkyl and aryl; or a pharmaceutically-acceptable salt or ester thereof.

A further preferred class of compounds within Formula I consists of those compounds wherein $R^1$ is selected from hydrido, alkyl and phenalkyl; wherein each of $R^2$ and $R^3$ is independently selected from hydrido, halo, hydroxy, alkyl, haloalkyl, alkoxy, hydroxyalkyl, phenalkyl, amino, moncalkylamino, dialkylamino, and phenyl; wherein each of $R^4$ through $R^7$ is independently selected from hydrido, halo, hydroxy, alkyl, haloalkyl, alkoxy, hydroxyalkyl, phenalkyl, phenoxy, benzyloxy, phenethyloxy, amino, monoalkylamino, dialkylamino, acyloxy, phenyl and

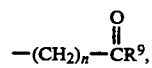

wherein $R^9$ is selected from hydrido, hydroxy, alkyl, alkoxy, phenyl, phenoxy, phenalkyl, phenalkyloxy, amino, monoalkylamino and dialkylamino, wherein n is a number selected from zero through four; wherein X is selected from amino, monoalkylamino, dialkylamino and $OR^{10}$ wherein $R^{10}$ is selected from hydrido, halo, alkyl, phenalkyl and phenyl; wherein Y is selected from hydroxy, halo, alkoxy and

wherein $R^{11}$ is selected from hydrido, hydroxy, alkyl, alkoxy, phenyl, phenoxy, phenalkyl, phenalkyloxy, amino, monoalkylamino and dialkylamino; wherein m is a number selected from zero through six; and wherein any of the foregoing X, Y and $R^1$ through $R^{11}$ substituents having a substitutable position is substituted with a radical selected from alkyl, hydroxy, alkoxy, amino, monoalkylamino, dialkylamino, monophenalkylamino, phenalkyl and phenyl; or a pharmaceutically-acceptable salt or ester thereof.

A more preferred class of compounds within Formula I consists of compounds wherein $R^1$ is selected from hydrido and lower alkyl; and wherein each of $R^2$ and $R^3$ is independently selected from hydrido, halo, lower alkyl, benzyl and phenyl; wherein each of $R^4$ through $R^7$ is independently selected from hydrido, halo, hydroxy, lower alkyl, haloalkyl, lower alkoxy, phenoxy, benzyloxy, benzyl, phenyl, and

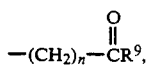

wherein $R^9$ is selected from hydrido, hydroxy, lower alkyl, lower alkoxy, phenyl, phenoxy, benzyl, benzyloxy, amino, monoalkylamino and dialkylamino, wherein n is a number selected from zero through two; wherein X is selected from amino, monoalkylamino, dialkylamino and $OR^{10}$ wherein $R^{10}$ is selected from hydrido, lower alkyl, benzyl and phenyl; wherein Y is selected from hydroxy, halo, lower alkoxy, benzyloxy and

wherein $R^{11}$ is selected from hydrido, hydroxy lower alkyl, lower alkoxy, phenyl, phenoxy, benzyl, benzyloxy, amino, monoalkylamino and dialkylamino; wherein m is a number selected from zero through four; and wherein any of the foregoing X, Y and $R^1$ through $R^{11}$ substituents having a substitutable position is substituted with a radical selected from lower alkyl, hydroxy, lower alkoxy, benzyl, amino, monoalkylamino, dialkylamino, monophenalkylamino and phenyl; or a pharmaceutically-acceptable salt or ester thereof.

A more highly preferred family of compounds consists of those compounds of Formula II:

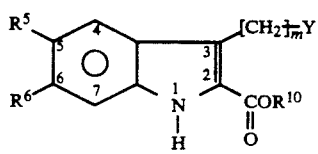

wherein each of $R^5$ and $R^6$ is independently selected from hydrido, halo, lower alkyl, haloloweralkyl and lower alkoxy; and wherein $R^{10}$ is selected from hydrido, lower alkyl, benzyl and phenyl; wherein Y is selected from hydroxy, lower alkoxy, benxyloxy and

wherein $R^{11}$ is selected from hydrido, hydroxy, lower alkyl, lower alkoxy, amino, monoalkylamino, dialkylamino, monophenalkylamino and phenyl; wherein m is one or two; or a pharmaceutically-acceptable salt thereof.

An even more highly preferred family of compounds consists of those compounds of Formula III:

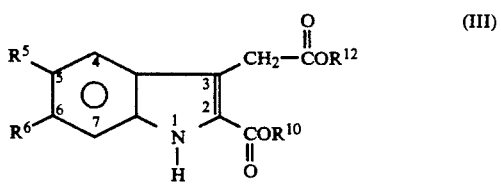

wherein each of $R^5$ and $R^6$ is independently selected from hydrido, fluoro, chloro and bromo; wherein $R^{10}$ is selected from hydrido and lower alkyl; wherein $R^{12}$ is selected from hydrido and lower alkyl; or a pharmaceutically-acceptable salt thereof.

A most highly preferred family of compounds consists of 2-carboxy-3-indoleacetic acid; 2-carboxy-1-methyl-3-indoleacetic acid; 2-carboxy-5-chloro-3-indoleacetic acid; 5-bromo-2-carboxy-3-indoleacetic acid; 2-carboxy-5-fluoro-3-indoleacetic acid; ethyl 2-carboxy-6-chloro-3-indoleacetate; 2-carboxy-6-chloro-3-indoleacetamide; 2-carboxy-6-chloro-3-indoleacetic acid 3-ethylamide; ethyl 6-chloro-3-(2-chloroethyl)-2-indolecarboxylate; and 2-carboxy-6-chloro-3-indoleacetic acid. Especially preferred of this family is 2-carboxy-6-chloro-3-indoleacetic acid.

The phrase "therapeutically-effective amount" means that amount of one or more compounds of Formula I which provides a therapeutic benefit in treatment or management of neurotoxic injury resulting from a CNS disorder or traumatic event or in treatment or management of a neurodegenerative disease. Examples of traumatic events which may result in neurotoxic injury are hypoxia, anoxia and ischemia associated with perinatal asphyxia, cardiac arrest or stroke. In treatment of such traumatic-event-related cases, a "therapeutically-effective amount" of a compound of Formula I would be an antineurotoxic or an antiexcitotoxic amount of the compound which is effective to reduce or prevent such neurotoxic injury by inhibiting, for example, excessive amounts of excitotoxin from being generated near or attaching to excitatory amino acid receptors. In cases of treatment of a neurodegenerative disease, the amount of a "therapeutically-effective amount" of a compound of Formula I would be that amount effective to reduce or prevent neurodegeneration arising from or causing CNS disorders such as convulsions and epilepsy.

The term "hydrido" denotes a single hydrogen atom (H) which may be attached, for example, to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to ten carbon atoms, such as cyclopropyl, cyclobutyl, cyclohexyl and cycloheptyl. An example of "cycloalkylalkyl" is cyclohexylmethyl. The term "haloalkyl "embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy" embraces linear or branched oxy-containing radicals having an alkyl portion of one to about ten carbon atoms, such as methoxy, ethoxy, isopropoxy and butoxy. An example of "cycloalkyloxy" is cyclohexyloxy. An example of "alkoxyalkyl" is methoxymethyl. An example of "aralkyloxy" is benzyloxy. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals =SO and =SO$_2$. The terms "monoalkylamino" and "dialkylamino" denote amino groups which have been substituted, respectively, with one alkyl radical and with two alkyl radicals. The terms "monoaralkylamino" and "diaralkylamino" denote amino groups substituted, respectively, with one and two aralkyl groups, an example of such aralkyl groups being phenalkyl such as benzyl or phenethyl. The term "acyl" whether used alone, or within a term such as acyloxy, denotes a radical provided by the residue after removal of hydroxyl from an organic acid, examples of such radical being acetyl and benzoyl.

Within this class of compounds of the invention are the pharmaceutically acceptable salts of the compounds of Formula I, including acid addition salts and base addition salts. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically-acceptable acid addition salts cf compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxy-ethanesulfonic, pantothenic, benzenesulfonic, toluenesulfonic, sulfanilic, mesylic, cyclohexylaminosulfonic, stearic, algenic, $\beta$-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form cf optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

General Synthetic Procedures

Generic Procedure I

Compounds of Formulas I-III may be prepared in accordance with the following general procedures:

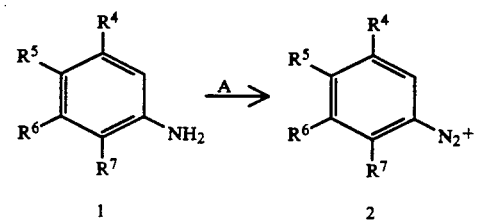

wherein R$^4$ through R$^7$ are as defined before; wherein A can be a variety of nitrite reagents such as sodium nitrite, amyl nitrite, or isoamyl nitrite.

One of the processes that can be used to synthesize the products of the invention starts with anilines of general structure 1 where $R^4$ through $R^7$ have the value assigned previously. The aniline is treated with the nitrite reagent in the presence of a variety of Bronsted acids like hydrochloric acid, trifluoroacetic acid or sulfuric acid to generate the diazonium salt of general structure 2. The reaction is best achieved by mixing the re agents in a solvent like water or mixtures of water and ethanol, methanol, acetonitrile or tetrahydrofuran. The reaction temperature can vary from about $-15°$ C. to room temperature.

wherein X, Y, m, and $R^2$ through $R^7$ are as defined before; wherein $R^{13}$ can be selected from hydrido, lower alkyl or benzyl.

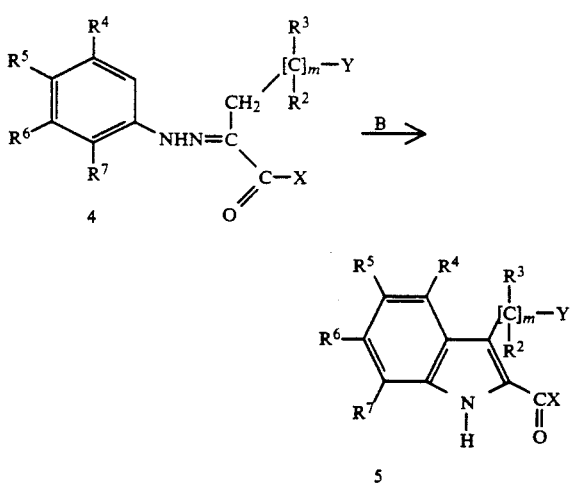

In the second step of the process, the diazonium salt 2 is transformed into the hydrazone 4 by mixing with the 2- acylester 3 in aqueous solvent. Possible aqueous solvents are water or mixtures of water and ethanol, methanol, acetonitrile or tetrahydrofuran.

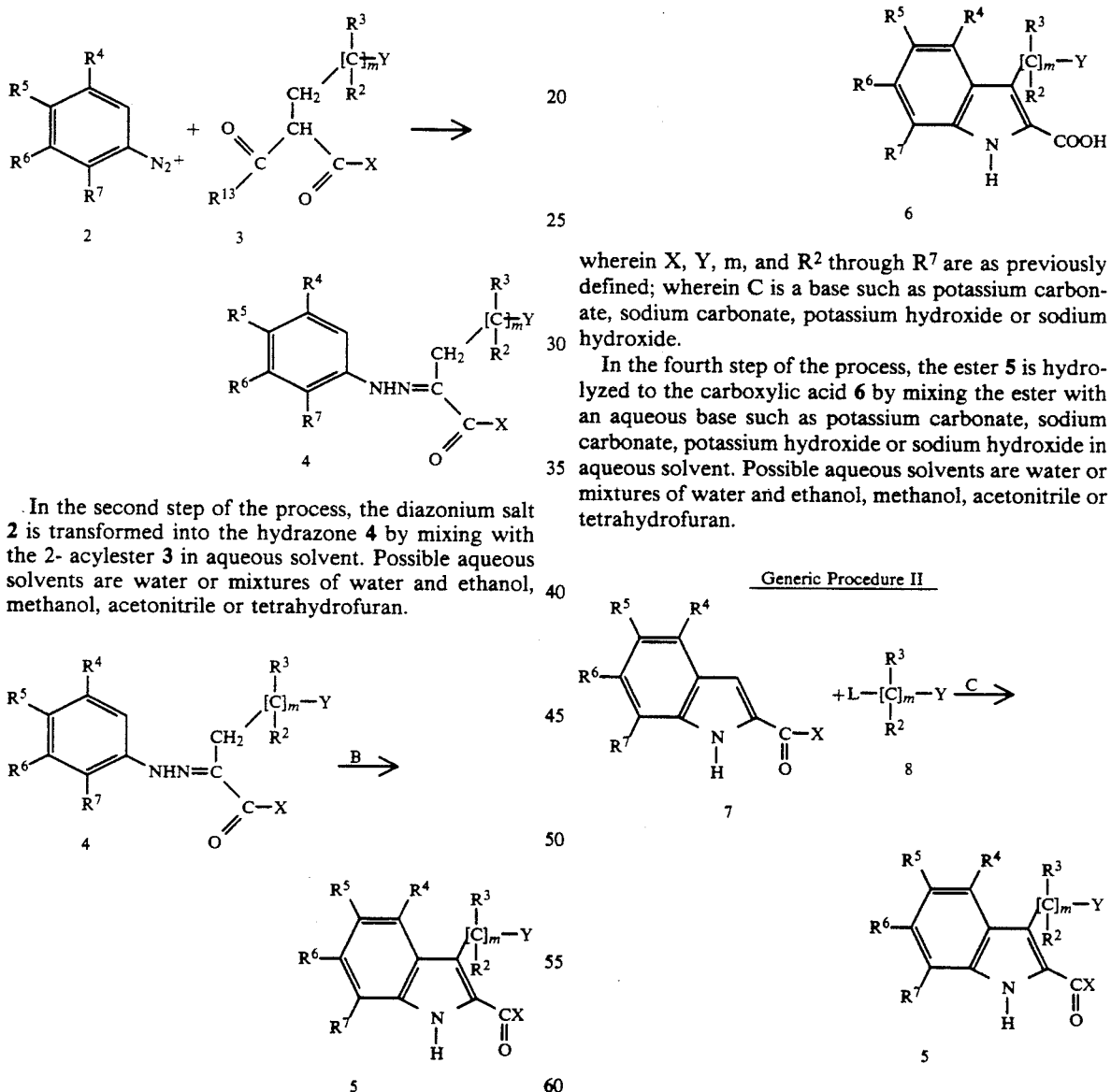

wherein X, Y, m, and $R^2$ through $R^7$ are as defined before; wherein B is a variety of Bronsted acids like hydrochloric acid, trifluoroacetic acid or sulfuric acid.

In the third step of the reaction, the hydrazone 4 is transformed into the indole of general structure 5. This conversion is best achieved by mixing the hydrazone in a protic solvent like ethanol, methanol, or water with a variety of Bronsted acids such as hydrochloric acid, trifluoroacetic acid or sulfuric acid. The reaction temperature can vary from room temperature to reflux of the reaction mixture.

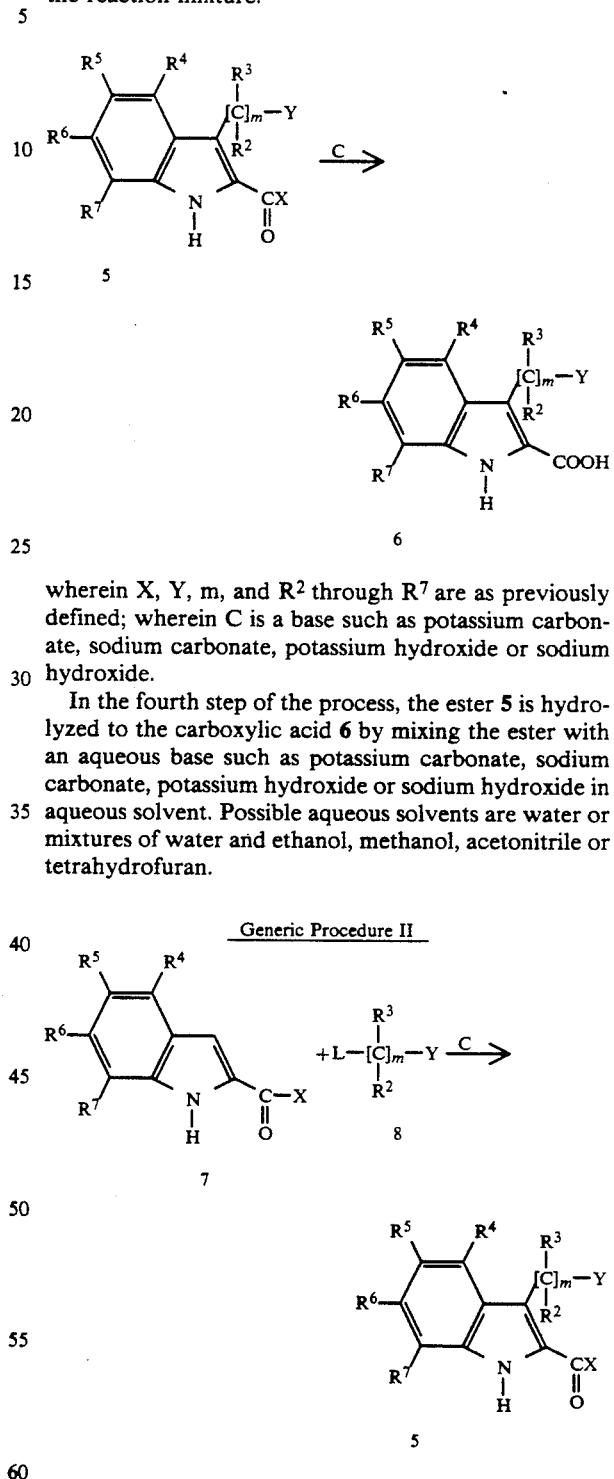

wherein X, Y, m, and $R^2$ through $R^7$ are as previously defined; wherein C is a base such as potassium carbonate, sodium carbonate, potassium hydroxide or sodium hydroxide.

In the fourth step of the process, the ester 5 is hydrolyzed to the carboxylic acid 6 by mixing the ester with an aqueous base such as potassium carbonate, sodium carbonate, potassium hydroxide or sodium hydroxide in aqueous solvent. Possible aqueous solvents are water or mixtures of water and ethanol, methanol, acetonitrile or tetrahydrofuran.

Generic Procedure II wherein C, X, Y, m, and $R^2$ through $R^7$ are as defined previously; wherein L is halogen, tosylate, mesylate, brosylate or OH.

The compounds of the invention may be prepared by displacement of the leaving group L in general structure 8 by the appropriate nucleophilic indole of general structure 7. Good leaving groups are, for example, halogen, tosylate, mesylate, and brosylate. The conversion can best be achieved by mixing the reagents in protic or aprotic solvents like ethanol, methanol, acetonitrile, acetone, or tetrahydrofuran in the presence of a base such as sodium or potassium carbonate or sodium or potassium hydroxide. The temperature of the reaction can vary from 0° C. to reflux of the reaction mixture.

Generic Procedure III

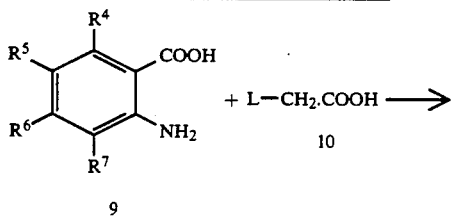

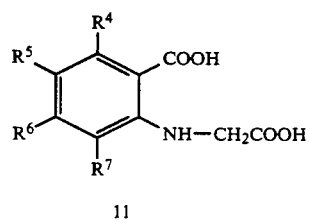

wherein L and $R^4$ through $R^7$ are as described previously.

The compounds of the invention may be prepared by displacement of the leaving group L in general structure 10 by the appropriate aniline 9. Good leaving groups are, for example, halogen, tosylate, mesylate, and brosylate. The conversion can best be achieved by mixing the reagents in protic or aprotic solvents like water, ethanol, methanol, acetonitrile, acetone, or tetrahydrofuran in the presence of a base such as sodium or potassium carbonate or sodium or potassium hydroxide. The temperature of the reaction can vary from 0° C. to reflux of the reaction mixture.

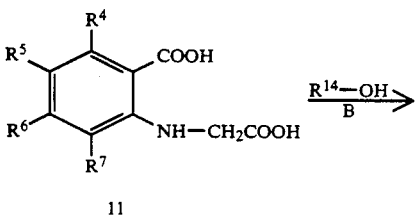

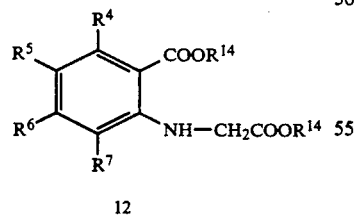

wherein B and $R^4$ through $R^7$ are as described previously; wherein $R^{14}$ is selected from-lower alkyl or benzyl.

In the second step of the process, the diacid 11 is converted to the diester 12 by mixing the diacid with an appropriate alcohol or phenol in the presence of an acid. The alcohol may be selected from a variety of lower alkyl alcohols, arylalkyl alcohols or phenols such as methanol, ethanol, benzyl alcohol or phenol. The diacid is treated with the alcohol in the presence of a variety of Bronsted acids like hydrochloric acid, trifluoroacetic acid or sulfuric acid to generate the diester of general structure 12. The reaction is best achieved by mixing the reagents neat or in an aprotic solvent such as ether, tetrahydrofuran, or acetonitrile. The reaction temperature can vary from about room temperature to reflux of the reaction mixture.

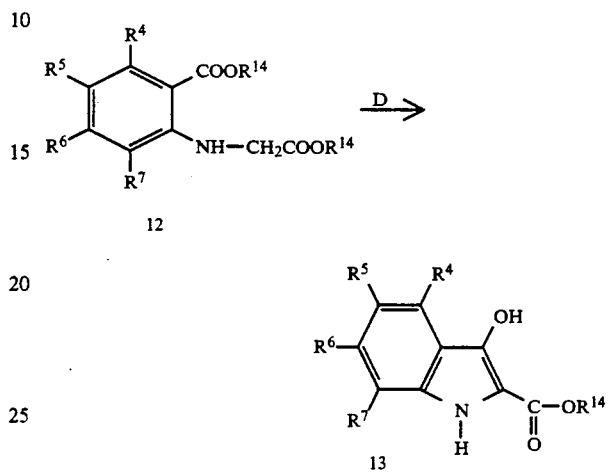

wherein $R^{13}$ and $R^4$ through $R^7$ are as described previously; wherein D can be selected from a variety of strong bases such as sodium methoxide, sodium ethoxide, potassium t-butoxide, or sodium hydride.

In the third step of the process, the diester of general structure 12 is mixed with an inert solvent like ether, tetrahydrofuran, or dioxane. The solution of the diester is added to a mixture of the base in the same inert solvent. The base can be selected from a variety of strong bases such as sodium methoxide, sodium ethoxide, potassium t-butoxide, or sodium hydride. The conversion can be achieved by varying the temperature from room temperature to reflux of the reaction.

Generic Procedure IV

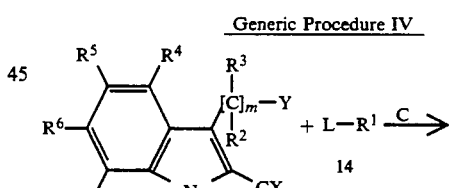

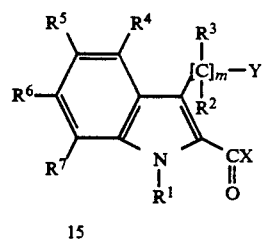

wherein C, L, m, X, Y, and $R^1$ through $R^7$ are as described previously.

The compounds of the invention may be prepared by displacement of the leaving group L in the general structure 14 by the indole of general structure 5. Good leaving groups are, for example, halogen, tosylate, mesylate and brosylate. The conversion can best be achieved by mixing the reagents in an aprotic solvent like tetrahydrofuran, acetonitrile, ether, or methylene chloride in the presence of a base such as sodium or potassium carbonate or sodium or potassium hydroxide. The temperature of the reaction can vary from room temperature to reflux of the reaction mixture.

The following Examples I-X are detailed descriptions of the methods of preparation of compounds of Formula I. These detailed preparations fall within the scope of, and serve to exemplify, the above described General Synthetic Procedures which form part of the invention. These Examples I-X are presented for illustrative purposes only and are not intended as a restriction on the scope of the invention. All parts are by weight unless otherwise indicated.

Example I

Phenylhydrazone of diethyl 2-ketoglutarate

Aniline (7.2 gm), in a mixture of concentrated hydrochloric acid (19 ml) and water (8 ml), was cooled in an ice bath and treated with a solution of sodium nitrite (5.3 gm) in water (15 ml). After the addition, the mixture was stirred in the ice bath until all solids had dissolved. The solution was then treated with a mixture of potassium hydroxide (17.2 gm), diethyl 2-acetoglutarate (17.7 gm), and ice (70 gm), and the resulting mixture stirred an additional 15 minutes. The mixture was acidified with concentrated hydrochloric acid and extracted with ether (5×120 ml). The ether solution was washed with 1N hydrochloric acid (2×120 ml), and water (120 ml), then dried over magnesium sulfate. The solvent was removed on a rotary evaporator to provide the hydrazone as a red oil.

EXAMPLE II

Ethyl 2-Carboethoxy-3-indoleacetate

The crude hydrazone of Example I was dissolved in absolute ethanol (50 ml), cooled in an ice bath, and treated with gaseous hydrogen chloride until saturated. The solution was heated to reflux for one hour, cooled to room temperature, and treated slowly with water (50 ml). The resulting mixture was extracted with ether (5×100 ml) and the combined ether solutions were washed with 5% sodium bicarbonate (3×250 ml) and water (3×250 ml). The ether solution was dried over magnesium sulfate and the solvent removed on a rotary evaporator to give the crude product as a brown oil. The crude material was placed on a silica gel 60 column and the product eluted with 30% ethyl acetate in hexane. After removal of the eluant on a rotary evaporator, the resulting brown solid was sublimed (85° C.@0.2 mm Hg) to give the product as a yellow solid (mp=75-78° C.).

EXAMPLE III

2-Carboxy-3-indoleacetic acid (Compound No. 1)

Ethyl 2-Carboethoxy-3-indoleacetate (0.7 gm) in absolute ethanol (10 ml) was combined with 50% aqueous sodium hydroxide. The mixture was heated to reflux on a steam bath for 15 minutes. The resulting solution was poured into water (50 ml) and the aqueous solution was washed with ether (2×30 ml). The aqueous solution was made acidic by the addition of concentrated hydrochloric acid and chilled to effect crystallization. The resulting white solid was recovered by filtration to provide the product. Analytical data are reported in Table I.

EXAMPLE IV

Ethyl 2-Carboethoxy-1-methyl-3-indoleacetate

Ethyl 2-Carboethoxy-3-indoleacetate (1 gm) in acetonitrile (50 ml) was combined with potassium carbonate (2 gm) and dimethyl sulfate (0.38 ml). The mixture was heated to reflux for 20 hours, filtered warm, and the solvent removed on the rotary evaporator. The residue was suspended in ether (150 ml) and the mixture washed with 5% hydrochloric acid (3×50 ml), 5% sodium bicarbonate (3×50 ml) and water (3×50 ml). The ether solution was dried over magnesium sulfate and the solvent removed on a rotary evaporator to provide the product.

EXAMPLE V

Ethyl 2-Carboethoxy-5-fluoro-3-indoleacetate

The 4-fluorophenylhydrazone of diethyl 2-ketoglutarate (45 mmoles) was combined with 20% sulfuric acid in absolute ethanol and heated to reflux for 9 hours. The solution was cooled to room temperature and cautiously poured onto ice (50 gm). The aqueous mixture was extracted with methylene chloride (3×50 ml) and the combined organic layers were washed with water (3×50 ml), 5% sodium bicarbonate (2×50 ml), and water (1×50 ml). The solution was dried over magnesium sulfate and the methylene chloride removed on the rotary evaporator. The residue was distilled on a Kugelrohr apparatus (140° C.@0.03 mm Hg) to provide an orange oil which solidified upon standing. This orange solid was recrystallized from a mixture of ethyl acetate and hexane to give the product as a yellow solid (mp=128-130° C.).

EXAMPLE VI

Ethyl 2-Carboethoxy-3-indolepropanoate

Ethyl 2-indolecarboxylate (3 gm), ethyl 3-iodopropanoate (5.4 gm), potassium carbonate (5 gm), and acetonitrile (50 ml) were combined and the mixture heated to reflux for 48 hours. The mixture was cooled and poured into water (50 ml). The mixture was extracted with ether (3×75 ml) and the combined ether extracts were washed with water (3×30 ml). The organic layer was dried over sodium sulfate and the solvent removed on a rotary evaporator. The diester product was obtained as a colorless oil.

EXAMPLE VII

N-(2-Carboxy-4-chlorophenyl)glycine

2-Amino-4-chlorobenzoic acid and chloroacetic acid were combined and neutralized by the careful addition of 1 N potassium carbonate solution. The mixture was heated to reflux and treated periodically with additional 1 N potassium carbonate to keep the mixture slightly basic. Reflux was continued until the solution remained basic for at least 45 minutes after the addition of the potassium carbonate solution. The mixture was cooled to room temperature, filtered through charcoal, and acidified with 1 N hydrochloric acid. The resulting white solid was filtered and dried under vacuum for 48 hours to provide the product.

EXAMPLE VIII

Dimethyl N-(2-Carboxy-4-chlorophenyl)glycinate

N-(2-Carboxy-4-chlorophenyl)glycine (4.5 gm) in methanol (50 ml) was treated slowly with sulfuric acid (6 ml). The solution was heated to reflux 20 hours. The resulting solid was filtered, washed with saturated aqueous sodium bicarbonate (75 ml) and water (75 ml), and dried under vacuum to provide the product.

EXAMPLE IX

6-Chloro-3-hydroxyindole-2-carboxylic acid (Compound No. 11)

Dimethyl N-(2-Carboxy-4-chlorophenyl)glycinate (3.4 gm) was combined with dry tetrahydrofuran (20 ml) and added dropwise to a mixture of potassium t-butoxide (1.9 gm) in dry tetrahydrofuran (30 ml). The resulting mixture was heated to reflux for 2 hours, cooled in an ice bath, then poured onto ice (325 gm). The aqueous mixture was acidified with acetic acid and the resulting precipitate was filtered, washed with water (50 ml) and air dried. The crude methyl ester (2.3 gm) was hydrolyzed without further purification to give the crude product by the procedure outlined in Example III. The product was purified using a DEAE Sepharose ion exchange column with a linear gradient of 00.5 N sodium bicarbonate. The appropriate factions were combined, the solution was made acidic by the addition of concentrated hydrochloric acid and the product extracted into ether (3×100 ml3. The ether solution was dried over magnesium sulfate and the ether removed on a rotary evaporator. The residue was dissolved in ethyl acetate and purified by preparative centrifugally accelerated radial thin layer chromatography on silica gel using ethyl acetate as eluant. The product was obtained as a yellow solid. Physical data are reported in Table I.

EXAMPLE X

3-Hydroxymethylindole-2-carboxylic acid (Compound No. 12)

Ethyl indole-2-carboxylate (5.87 gm) in absolute ethanol (85 ml) was combined with potassium carbonate (4.3 gm) and 37% formaldehyde (2.6 gm) and heated to reflux for four days. The mixture was cooled to room temperature and the solvents removed on a rotary evaporator. The residue was dissolved in water (100 ml) and the water solution was washed with ether (2×50 ml). The aqueous solution was made acidic with 3.6 N sulfuric acid and the resulting mixture was extracted with methylene chloride (2×50 ml) and ether (2×50 ml). The combined organic layers were dried over magnesium sulfate and the solvent removed on a rotary evaporator. The residue was dissolved in acetone and purified by preparative centrifugally accelerated radial thin layer chromatography on silica gel using 10% methanol in methylene chloride as eluant. The product was obtained as an off-white solid. Physical data are reported in Table I.

Table I lists compounds of Formula which can be prepared in accordance with the general and specific procedures described above, or which are known and can be purchased from commercial sources.

TABLE I

| Compound Number | Name | Structure | Elemental Theor. | Analysis Found | Melting Point |
|---|---|---|---|---|---|
| 1 | 2-carboxy-3-indoleacetic acid .0.1 H$_2$O | 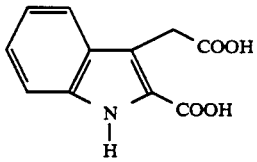 | C 59.71<br>H 4.20<br>N 6.33 | 59.71<br>4.18<br>6.28 | 225–227° C. |
| 2 | 2-carboxy-1-methyl-3-indole-acetic acid | 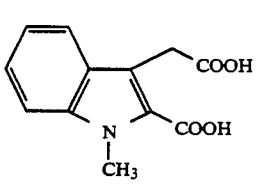 | C 61.79<br>H 4.75<br>N 6.00 | 61.48<br>4.80<br>5.91 | 236–238° C. |
| 3 | 2-carboxy-5-chloro-3-indole-acetic acid.0.8 acetone | 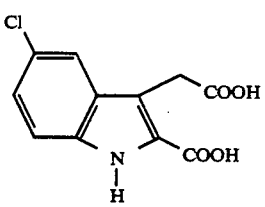 | C 53.69<br>H 4.34<br>N 4.63 | 53.56<br>4.42<br>4.49 | 274–279° C. |
| 4 | 5-bromo-2-carboxy-3-indole-acetic acid.0.9 acetone | 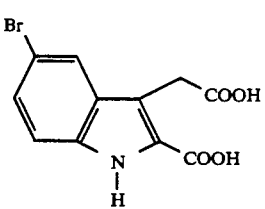 | C 46.85<br>H 3.81<br>N 4.03 | 46.83<br>3.79<br>3.91 | 269–271° C. |

TABLE I-continued

| Compound Number | Name | Structure | Elemental Theor. | Analysis Found | Melting Point |
|---|---|---|---|---|---|
| 5 | 2-carboxy-5-fluoro-3-indole-acetic acid | 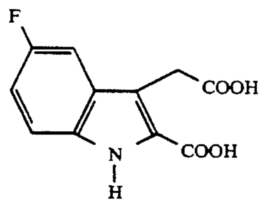 | C 55.70<br>H 3.40<br>N 5.91 | 55.41<br>3.72<br>5.61 | 252–254° C. |
| 6 | 2-carboxy-6-chloro-3-indole-acetic acid | 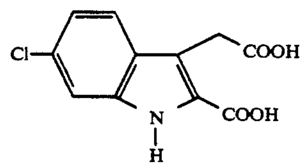 | C 52.09<br>H 3.18<br>N 5.52 | 51.99<br>3.27<br>5.28 | 257–259° C. |
| 7 | 2-carboxy-3-indolepropanoic acid.0.3 H$_2$O | 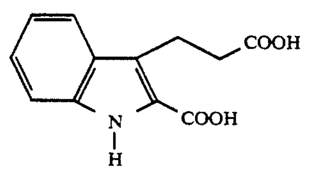 | C 60.40<br>H 4.89<br>N 5.86 | 60.12<br>4.68<br>5.85 | 218–220° C. |
| 8 | 2-carboxy-3-indolebutanoic acid.0.2 H$_2$O | 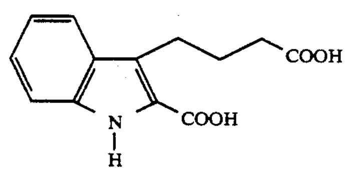 | C 62.24<br>H 5.38<br>N 5.58 | 62.09<br>5.28<br>5.52 | 184–186° C. |
| 9 | 2-carboxy-3-indolepentanoic acid.0.1 H$_2$O | 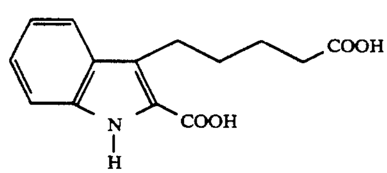 | C 63.91<br>H 5.82<br>N 5.32 | 63.96<br>5.87<br>5.27 | 144–145° C. |
| 10 | 2-(2-carboxy-3-indole)butanoic acid | 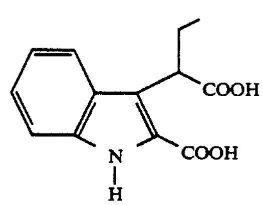 | C 62.24<br>H 5.38<br>N 5.58 | 62.01<br>5.32<br>5.44 | 174–177° C. |
| 11 | 6-chloro-3-hydroxyindole-2-carboxylic acid | 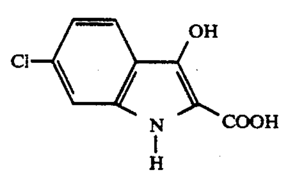 | — | — | 232–234° C. |
| 12 | 3-hydroxymethylindole-2-carboxylic acid | 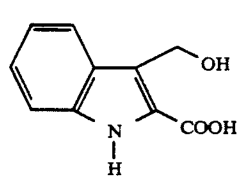 | — | — | 226–230° C. (dec.) |

TABLE I-continued

| Compound Number | Name | Structure | Elemental Theor. | Analysis Found | Melting Point |
|---|---|---|---|---|---|
| 13 | indole-2-carboxylic acid | 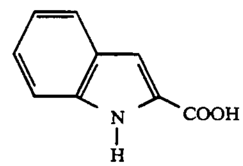 | — | — | 205–208° C. |
| 14 | 5-chloroindole-2-carboxylic acid | 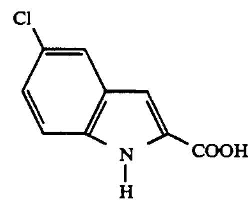 | — | — | 286–287° C. |
| 15 | 5-fluoroindole-2-carboxylic acid | 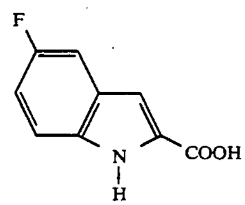 | — | — | 258–259° C. |
| 16 | 5-bromoindole-2-carboxylic acid | 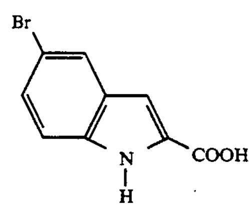 | — | — | 280–281° C. (dec.) |
| 17 | 5-methylindole-2-carboxylic acid | 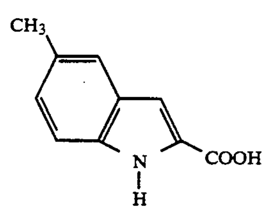 | — | — | 246–248° C. |
| 18 | 5-methoxyindole-2-carboxylic acid | 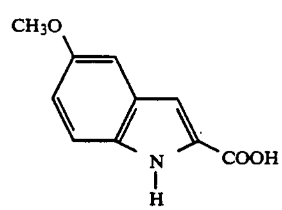 | — | — | 199–201° C. |
| 19 | ethyl 2-carboethoxy-3-indoleacetate | 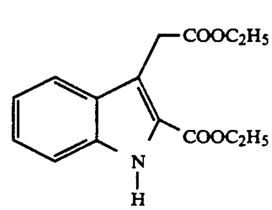 | C 65.44<br>H 6.22<br>N 5.09 | 65.33<br>6.27<br>5.19 | 77–78° C. |

TABLE I-continued

| Compound Number | Name | Structure | Elemental Analysis Theor. | Found | Melting Point |
|---|---|---|---|---|---|
| 20 | 3-(2-hydroxyethyl)indole-2-carboxylic acid | 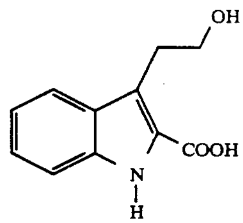 | C 64.38<br>H 5.40<br>N 6.83 | 64.18<br>5.66<br>6.63 | 196–198° C. |
| 21 | 2-carboxy-6-chloro-5-methylindole-3-acetic acid .0.4 H$_2$O | 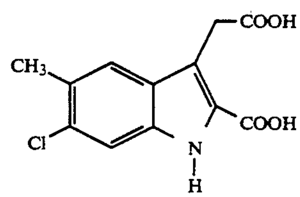 | C 52.51<br>H 3.95<br>N 5.10 | 52.56<br>4.05<br>4.80 | 265–269° C. (dec.) |
| 22 | ethyl 2-carboethoxy-6-chloro-3-indoleacetate | 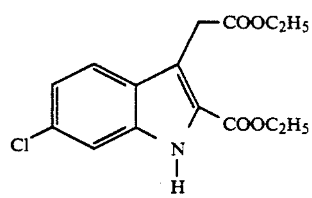 | C 58.17<br>H 5.21<br>N 4.52 | 58.30<br>5.15<br>4.44 | 143–145° C. |
| 23 | 4,9-dihydropyrano[3,4-b]indol-1(3H)-one.0.2H$_2$O | 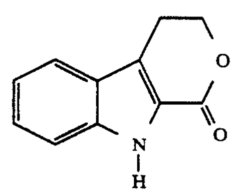 | C 69.45<br>H 4.95<br>N 7.36 | 69.49<br>5.09<br>7.06 | 195–196° C. |
| 24 | 3-formylindole-2-carboxylic acid.0.1 ethyl acetate | 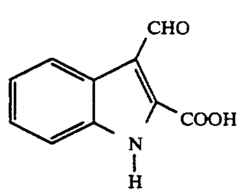 | C 63.01<br>H 4.02<br>N 7.01 | 62.89<br>3.88<br>7.05 | 245–247° C. |
| 25 | 3-(2-oxopropyl)indole-2-carboxylic acid | 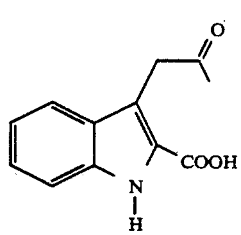 | C 66.35<br>H 5.10<br>N 6.45 | 66.0<br>5.17<br>6.42 | 166–168° C. |
| 26 | 4-carboxyindole-2-carboxylic acid.0.5H$_2$O | 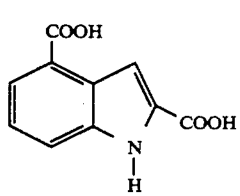 | C 55.89<br>H 3.79<br>N 6.52 | 55.83<br>3.27<br>6.48 | 324–328° C. |

TABLE I-continued

| Compound Number | Name | Structure | Elemental Theor. | Analysis Found | Melting Point |
|---|---|---|---|---|---|
| 27 | 4-benzyloxyindole-2-carboxylic acid | 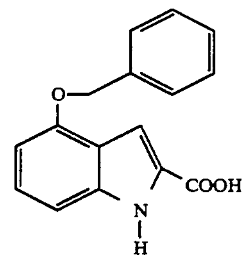 | C 71.90<br>H 4.90<br>N 5.24 | 71.60<br>4.79<br>5.16 | 245–249° C. (dec.) |
| 28 | 4-hydroxyindole-2-carboxylic acid.0.1H$_2$O | 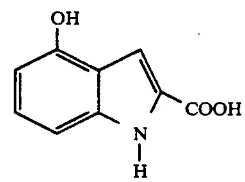 | C 60.53<br>H 4.04<br>N 7.84 | 60.58<br>4.18<br>7.60 | 255–258° C. (dec.) |
| 29 | 2-carboxy-7-chloroindole-3-acetic acid.0.8H$_2$O | 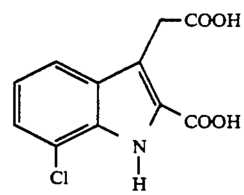 | C 49.37<br>H 3.60<br>N 5.23 | 49.29<br>3.02<br>5.19 | 262–264° C. (dec.) |
| 30 | 6-chloroindole-2-carboxylic acid.0.1H$_2$O | 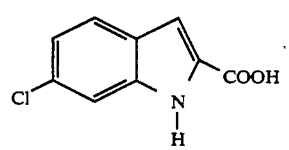 | C 54.78<br>H 3.16<br>N 7.10 | 54.77<br>3.04<br>7.06 | 254–256° C. (dec.) |
| 31 | ethyl 2-carboxy-6-chloro-3-indoleacetate | 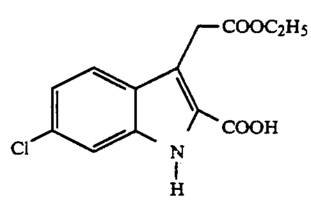 | C 55.43<br>H 4.29<br>N 4.97 | 55.04<br>4.30<br>4.95 | 243–245° C. (dec.) |
| 32 | 2-carboethoxy-6-chloro-3-indole acetic acid | 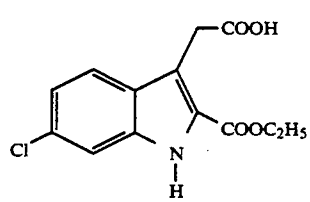 | C 55.43<br>H 4.29<br>N 4.97 | 55.04<br>4.30<br>4.96 | 243–245° C. (dec.) |
| 33 | 7-chloro-4,9-dihydropyrano-[3,4-b]indole-1,3-dione | 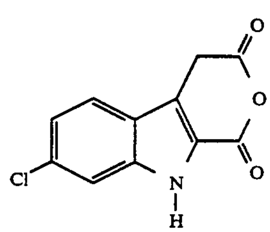 | C 56.07<br>H 2.57<br>N 5.94 | 55.80<br>2.80<br>5.94 | 209–220° C. (dec.) |

TABLE I-continued

| Compound Number | Name | Structure | Elemental Analysis Theor. | Found | Melting Point |
|---|---|---|---|---|---|
| 34 | ethyl 2-(3-dimethylamino-propyloxycarbonyl)-6-chloro-3-indole acetate | (structure) | C 58.93<br>H 6.32<br>N 7.64 | 58.67<br>6.32<br>7.59 | 105–106° C. |
| 35 | 2-propyl 2-carboxy-6-chloro-3-indoleacetate.1.1$H_2O$ | (structure) | C 53.29<br>H 5.17<br>N 4.44 | 53.01<br>4.64<br>4.41 | 225–233° C. (dec.) |
| 36 | 2-carboxy-6-chloro-3-indole acetic acid 3-dimethyl amide.0.35$H_2O$ | (structure) | C 54.40<br>H 4.81<br>N 9.76 | 55.39<br>4.55<br>9.66 | 268–272° C. (dec.) |
| 37 | 2-carboxy-6-chloro-3-indole-acetamide | (structure) | C 52.29<br>H 3.59<br>N 11.09 | 52.24<br>3.57<br>10.88 | 257–275° C. (dec.) |
| 38 | 2-carboxy-6-chloro-3-indole-acetic acid 3-methylamide | (structure) | — | — | 230–233° C. (dec.) |
| 39 | 2-carboxy-6-chloro-3-indole-acetic acid 3-(2-hydroxy-ethyl)amide | (structure) | — | — | 241–247° C. (dec.) |
| 40 | 2-carboxy-6-chloro-3-indole-acetic acid 3-(3-dimethyl-aminopropyl)amide | (structure) | — | — | 130–140° C. |

TABLE I-continued

| Compound Number | Name | Structure | Elemental Analysis Theor. | Found | Melting Point |
|---|---|---|---|---|---|
| 41 | methyl 2-carboxy-6-chloro-3-indole acetate.0.15H$_2$O | 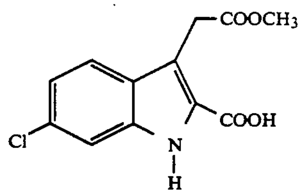 | C 53.85<br>H 3.84<br>N 5.18 | 53.33<br>4.01<br>4.97 | 230–232° C. |
| 42 | propyl 2-carboxy-6-chloro-3-indoleacetate.0.4H$_2$O | 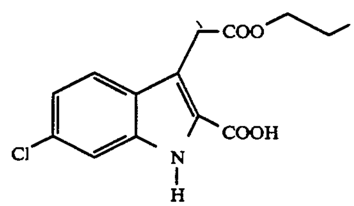 | C 55.51<br>H 4.92<br>N 4.62 | 55.48<br>4.73<br>4.58 | 206–212° C. (dec.) |
| 43 | 2-carboxy-6-chloro-3-indole-acetic acid 3-ethylamide | 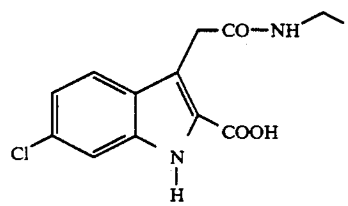 | C 55.62<br>H 4.67<br>N 9.98 | 55.43<br>4.72<br>9.71 | 230–231° C. (dec.) |
| 44 | 2-carboxy-6-chloro-3-indole-acetic acid 3-propylamide | 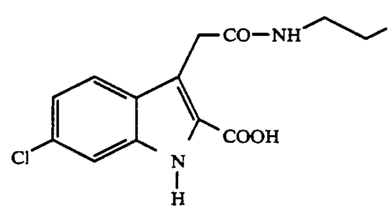 | C 57.05<br>H 5.13<br>N 9.50 | 56.76<br>5.09<br>9.26 | 232–233° C. (dec.) |
| 45 | 2-carboxy-6-chloro-3-indole-acetic acid 3-phenylethyl-amide.0.3H$_2$O | 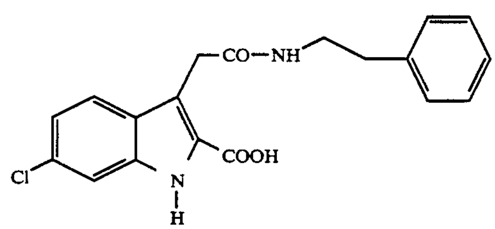 | C 63.36<br>H 4.37<br>N 7.78 | 63.57<br>4.77<br>7.71 | 187–191° C. |
| 46 | 6-chloro-3-(2-hydroxyethyl)-2-indolecarboxylic acid.H$_2$O | 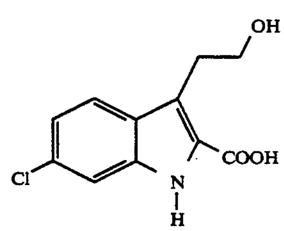 | C 51.27<br>H 4.69<br>N 5.44 | 51.27<br>4.33<br>5.32 | 176° C. |
| 47 | ethyl 6-chloro-3-(2-chloro-ethyl)-2-indolecarboxylate | 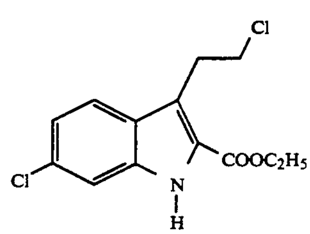 | C 54.57<br>H 4.58<br>N 4.89 | 54.58<br>4.57<br>4.88 | 171° C. |

TABLE I-continued

| Compound Number | Name | Structure | Elemental Theor. | Analysis Found | Melting Point |
|---|---|---|---|---|---|
| 48 | 6-chloro-3-(2-chloroethyl)-2-indolecarboxylic acid | 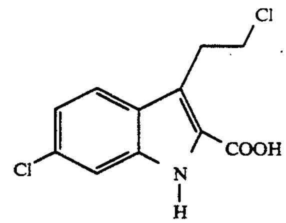 | — | — | 128° C. |
| 49 | 6-chloro-3-(2-ethoxyethyl)-2-indolecarboxylic acid | 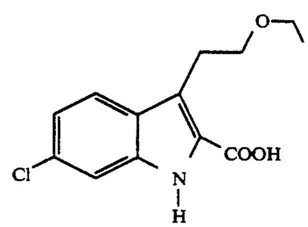 | — | — | 142° C. |
| 50 | ethyl 4-chloro-3-(2-chloroethyl)-2-indolecarboxylate | 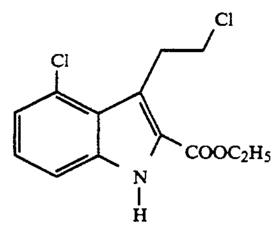 | C 54.57<br>H 4.58<br>N 4.89 | 54.49<br>4.47<br>4.87 | 158° C. |
| 51 | ethyl 6-chloro-2-formyl-3-indole acetate | 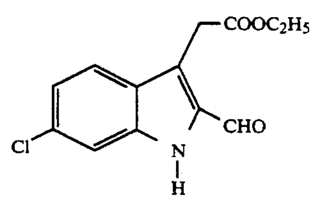 | — | — | 121–123° C. |
| 52 | ethyl 6-chloro-2-hydroxymethyl-3-indoleacetate | 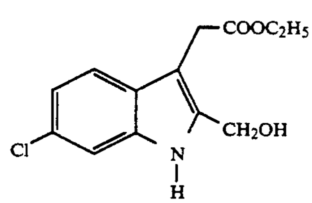 | C 58.33<br>H 5.27<br>N 5.23 | 58.16<br>5.40<br>5.15 | 118–120° C. |
| 53 | sodium 6-chloro-2-hydroxymethyl-3-indole-acetate.0.65NaOH | 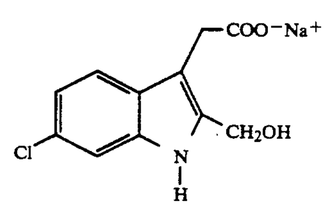 | C 45.93<br>H 3.38<br>N 4.87 | 46.04<br>3.28<br>4.82 | 225–235° C. (dec.) |
| 54 | 2-carboxy-6-chloro-3-indole acetic acid bis-2-dimethyl aminoethylamide | 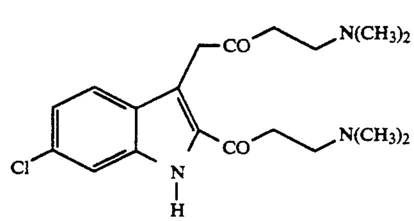 | C 57.93<br>H 7.16<br>N 17.78 | 57.70<br>7.06<br>17.59 | 166–168° C. |

TABLE I-continued

| Compound Number | Name | Structure | Elemental Theor. | Analysis Found | Melting Point |
|---|---|---|---|---|---|
| 55 | 2-carboethoxy-6-chloro-3-indoleacetamide | 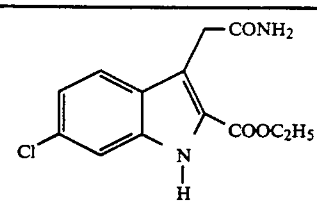 | C 55.62<br>H 4.67<br>N 9.98 | 55.24<br>4.59<br>9.78 | 229-230° C. |
| 56 | 7-chloro-4,9-dihydropyrano-[3,4-b]indole-1(3H)-one | 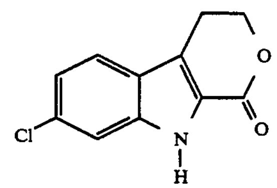 | C 59.61<br>H 3.64<br>N 6.32 | 59.45<br>3.75<br>6.24 | 240° C. |
| 57 | 5-chloro-4,9-dihydropyrano[3,4-b]idol-1(3H)-one | 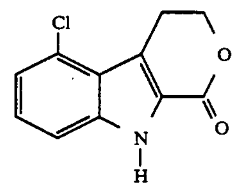 | C 59.61<br>H 3.64<br>N 6.32 | 59.43<br>3.70<br>6.28 | 229° C. |

BIOLOGICAL EVALUATION

Glutamate Binding Assays

The purpose of this assay is to determine the binding affinity of a compound of Formula I for the N-methyl-D-aspartate (NMDA) receptor site. This procedure was carried out as follows:

Synaptic plasma membranes (SPM) were prepared as previously described [Monahan, J. B. and Michel, J., "Identification and Characterization of an N-methyl-D-aspartate-specific L-[³H]glutamate Recognition Site in Synaptic Plasma Membranes, J. Neurochem., 48, 1699-1708 (1987)]. The SPM were stored at a concentration of 10-15 mg/ml in 0.32 M sucrose, 0.5 mM EDTA, 1 mM MgSO$_4$, 5 mM Tris/SO$_4$, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", Anal. Biochem., 86, 193-197 (1978)]. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation, and centrifugation was repeated a total of three times. This general method involved adding 12.5 nM of the L-[³H]glutamate radioligand to the appropriate concentration of the test compound and initiating the assay by the addition of ice cold SPM (0.2-0.45 mg). The binding assays were performed in 1.5 ml centrifuge tubes with the total volume adjusted to 1.0 ml. Additions of test compounds were made in 50 mM Tris/acetate, pH 7.4 and incubations were carried out at 0°-4° C. The incubation time for the NMDA binding assay was 10 minutes. To terminate the incubation, the samples were centrifuged for 15 minutes at 12,000 g and 4° C. in a Beckman Microfuge 12. The supernatant was aspirated and the pelleted membranes dissolved in Beckman Ready-Protein scintillation cocktail and the samples counted on a Beckman LS 5800 or 3801 liquid scintillation counter with automatic corrections for quenching and counting efficiency. Nonspecific binding was defined as the residual binding in the presence of 0.5 mM NMDA and was typically 15-25% of the total binding in the NMDA binding assay. Radioligand binding to the SPM was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", Computer Appln. Biosci., 3 131 (1987)]. Binding results are reported in Table II for example compounds of the invention.

Glycine Binding Assay Procedure

Synaptic plasma membranes (SPM) were prepared from rat forebrain and stored as previously described [J. B. Monahan and J. Michel, J. Neurochem, 48, 1699-1708 (1987)]. Frozen membranes were thawed and diluted 1:20 with 0.04% triton X-100 in 50 mM tris/acetate (pH 7.4). Following incubation at 37° C. for 30 min., the SPM were collected by centrifugation at 95,000 X g for 15 min. The pellet was resuspended in 50 mM tris/acetate (pH 7.4, triton-free) and hand-homogenized five times. The membranes were again centrifuged as above. The pellet was washed two additional times with 50 mM tris/acetate (without homogenization) and centrifuged. The final pellet was resuspended with homogenization in 50 mM tris/acetate.

In the general receptor binding assay procedure, 10 nM [³H]glycine was added to the appropriate concentration of the test compounds and the assay initiated by the addition of 0.2-0.4 mg of ice cold SPM. The assay, which was done in 1.5 ml centrifuge tubes, was adjusted to a total volume of 1.0 ml with all additions being made in 50 mM tris/ acetate, pH 7.4 at 4° C. After a 10 minute incubation at 2° C., the samples were centrifuged for 15 min. at 12,000 g (4° C.) in a Beckman Microfuge 12. The supernatant was aspirated and the tube tip containing the pelleted membranes cut off and agitated in 0.5 ml of Beckman BTS-450 tissue solubilizer for a minimum of 6 hours at room temperature. Beckman MP scintillation cocktail (5 ml) containing 7 ml/liter acetic acid was then added and the samples counted on a Beckman LS 5800 liquid scintillation counter with automatic corrections for quenching and counting efficiency. Nonspecific binding was defined as the residual binding in the presence of 0.1 mM glycine and usually amounted to 25-35% of the total binding. The binding of [$^3$H]glycine to the SPM was analyzed using Scatchard and Hill transformations and the $K_i$ for other compounds was determined using logit-log analysis. Calculations and regression analysis were performed using templates developed for Lotus 123 as previously described [Pullan et al, Id.]. Binding results are reported in Table II for example compounds of the invention.

TABLE II

| Test Compound No. | $K_i$ apparent NMDA* | (μM) Gly |
|---|---|---|
| 1 | 56.0 | 24.8 |
| 2 | >100 | >100 |
| 3 | >100 | 11.7 |
| 4 | >100 | 26.2 |
| 5 | >100 | 17.5 |
| 6 | >100 | 1.3 |
| 7 | >100 | >100 |
| 8 | >100 | >100 |
| 9 | >100 | >100 |
| 10 | >100 | >100 |
| 11 | >100 | >100 |
| 12 | >100 | >100 |
| 13 | >100 | >100 |
| 14 | >100 | >100 |
| 15 | >100 | 91.0 |
| 16 | >100 | >100 |
| 17 | >100 | >100 |
| 18 | >100 | >100 |
| 19 | >100 | >100 |
| 20 | — | >10 |
| 21 | — | >10 |
| 22 | — | >100 |
| 23 | — | >100 |
| 24 | >100 | 11.2 |
| 25 | — | >30 |
| 26 | — | >20 |
| 27 | — | >20 |
| 28 | — | >20 |
| 29 | — | >30 |
| 30 | — | 10.0 |
| 31 | >100 | 0.47 |
| 32 | — | 20.9 |
| 33 | — | 75.1 |
| 34 | — | >30 |
| 35 | — | 3.9 |
| 36 | — | >30 |
| 37 | — | 1.2 |
| 38 | — | 0.92 |
| 39 | — | 11.4 |
| 40 | — | >30 |
| 41 | — | 1.56 |
| 42 | — | 7.0 |
| 43 | — | 0.70 |
| 45 | — | 0.47 |
| 46 | — | 11.4 |
| 47 | — | >10 |
| 48 | — | 13.2 |
| 51 | — | >30 |
| 52 | — | >30 |
| 53 | — | >30 |
| 54 | — | >30 |

TABLE II-continued

| Test Compound No. | $K_i$ apparent NMDA* | (μM) Gly |
|---|---|---|
| 55 | — | >30 |

*— = Not Determined

Tissue Protection Assays

I. Xenopus Oocytes

PolyA+ RNA (mRNA) was extracted from adult male rat cortex using the refined guanidinium thiocyanate method developed by Han et al [J. H. Han et al., Biochemistry, 26, 1617-1625 (1987)] and the oligo (dT) cellulose chromatography procedure of Adiv and Leder [H. Aviv et al., Proc. Nat. Acad. Sci., 69, 1408-1412 (1972)]. Aliquots of mRNA (1.0 mg/ml water) were stored at −20° C.

Gravid adult female Xenopus laevis (Xenopus One, Ann Arbor, Mich. or NASCO, Ft. Atkinson, Wis.) were anaesthetized with 0.2% (w/v) Tricaine (3-amino benzoic acid ethyl ester; Sigma) and subjected to partial ovarectomy. Excised oocytes were then prepared and microinjected [N. W. Kleckner et al, Science 241 835-837 (1988)]. Oocytes were treated for one hour in Barth's solution (88.0 mM NaCl, 1.0 mM KCl, 2.4 mM NaHCO$_3$, 0.41 mM CaCl$_2$, 0.82 mM MgSO$_4$, 10.0 μg/ml penicillin, 100.0 μg/ml streptomycin, 10.0 mM HEPES, pH 7.5) containing 1.5 mg/ml Neutral Protease (Beohringer Mannheim Biochemicals, Grade II). Oocytes were then placed in Barth's solution containing 100.0 mM sucrose and manually defolliculated with fine forceps. Defolliculated oocytes were then microinjected with approximately 50 ng of mRNA in Barth's solution at 16°-18°·C.

Oocytes were assayed 2-8 days later for rat brain receptor expression via single electrode voltage. clamp (Axoclamp 2A, Axon Instruments) in a manner similar to that previously described [Kleckner et al, Id.]. Cells exhibiting stable resting membrane potentials of > −50 mV were voltage clamped to −60 mV in modified frog ringer's solution (116.0 mM NaCl, 2.0 mM KCl, 1.8 mM CaCl$_2$, 10.0 mM HEPES and zero added Mg$^{+2}$, pH 7.5) which was continuously perfused (5.0 ml/minute) at room temperature (22°-24° C.). Drugs were added to the perfusate and inward currents induced by agonist compounds were measured at peak steady state response. Maximal responses to NMDA in the presence of 10 μM glycine ranged from 3.0 to 50.0 nA and were typically 10 nA. No pharmacological difference between oocytes exhibiting lower and greater amplitude maximal responses was noted. Antagonist compounds were perfused for a minimum of 3.0 minutes prior to subsequent agonist co-application. Data are expressed as percent maximal response (mean±S.E.M.). Half-maximal responses (EC$_{50}$'s) and slopes for dose response data were determined from the least squares fit to the logistic regression equation. The IC$_{50}$ values for selected compounds in blocking the effects of various concentration of glycine are shown in Table III.

TABLE III

| | Glycine Blocking Effects** | | |
|---|---|---|---|
| Compound No. | 0.1 μM Gly | 1.0 μM Gly | 10 μM Gly |
| 6 | 0.77 ± 0.12 | 3.2 ± 1.1 | 6.1 ± 3.2 |
| 31 | —* | 1.6 ± 0.01 | 16.1 ± 1.4 |
| 35 | —* | 4.5 ± 0.5 | 68.5 ± 13.5 |

TABLE III-continued

Glycine Blocking Effects**

| Compound No. | 0.1 μM Gly | 1.0 μM Gly | 10 μM Gly |
|---|---|---|---|
| 37 | —* | 3.4 ± 0.9 | —* |

—* = Not Determined
**IC$_{50}$ (μM) values for selected compounds in blocking the effects of various concentrations of glycine in the presence of 100 μM NMDA.

II. Epileptic Hippocampal Slice

Hippocampal slices (450 μ) were obtained from male Sprague-Dawley albino rats (100–325 g). The method of slice preparation has been detailed elsewhere [A. H. Ganong et al., Brain Res., 273, 170–174 (1983)]. Slices were stored in a humidified interface chamber at room temperature and bathed in artificial cerebrospinal fluid (ACSF) which contained (in mM): NaCl 124.0, KCl 5.0, KH$_2$PO$_4$ 1.0, NaHCOP$_3$ 26.4, CaCl$_2$, 2.0, MgSO$_4$ 1.5 and D-glucose 10.0, and was equilibrated with 95% O$_2$:5% CO$_2$. When needed for study, slices were placed one at a time in a small submersion chamber maintained at 35° C. where they were continuously perfused at 1.0–2.0 ml/min. Fresh solutions reached the recording chamber within 20 seconds and the perfusate was completely changed over within a minute. Additional oxygen and stirring was provided by an air jet (95% O$_2$:5% CO$_2$) directed at the surface of the ACSF. Standard electrophysiological techniques were employed. Extracellular recording electrodes were glass micropipettes filled with 2.0 M NaCl and broken back to 2.0 mΩ resistance. All recording was from the somatic region of CA1. Slices employed in extracellular experiments described here exhibited a single population spike upon stimulation of the Schaffer collateral/commissural fibers in ACSF. Intracellular recording electrodes of 60–100 MQ resistance were filled with 2.5 M KAc. Intracellular data is from cells which exhibited a stable resting membrane potential of greater than −55 mV and upon stimulation fired action potentials which overshot zero mV potential and were less than 2 msec in duration. The Schaffer collateral/commissural fibers were stimulated with tungsten bipolar stimulating electrodes at a rate of 0.03 Hz. The resulting field EPSP (S/C-CA1 EPSP) and the DC potential were amplified by an Axoprobe 1 amplifier and were continuously monitored on a Tektronix 5111A storage oscilloscope and a Gould 2300 chart recorder with a Gould Waveform storage module. Epileptiform activity was induced by omission of Mg++ ions from the perfusate, which removes the Mg++ mediated voltage-dependent block of the NMDA. receptor [B. Ault et al., J. Physiol., 307, 413–428 (1980)], or by the addition of the GABA antagonist picrotoxin. Drugs were added to the perfusate and zero magnesium refers to solutions which contain no added magnesium. The amplitude of the stimulus evoked primary population spike was used to assess the effects of experimental manipulations on the efficacy of synaptic function. Results are shown in Table IV

TABLE IV

Effect of 30 μM Compound No. 6 and 300 μM Compound No. 35 vs. 0% Mg$^{+2}$-induced epilepsy in the in vitro hippocampal slice

| Parameter | Compound No. 6 % Control | Compound No. 35 % Control |
|---|---|---|
| Primary population spike amplitude | 97 | 82.1 |
| Sum of additional popula-tion spike amplitude | 70.1 | 35.6 |
| Burst duration | 60 | 19.2 |
| Spontaneous activity | 48 | 0 |

Assay for Effect on cGMP

Male Swiss Hausche mice (25–30 g) were injected intracisternally (i.c.t.) with glycine agonists 10 minutes prior to sacrifice by focussed microwave irradiation. Compounds of the invention were injected intracisternally 2 minutes prior to the agonist. For intracisternal injections, al agonists were dissolved in HCl and diluted with isotonic saline prior to adjustment of the pH to between 6 and 7 with NaOH. The compounds of the invention were dissolved in isotonic saline and all compounds were administered in a volume of 5 μl. The agonist doses were obtained by making serial dilutions of a concentrated solution of drug until intracisternal injections of 5 μl resulted in no more than 10% mortality during the first 15 minutes after injection.

Hydrochloric acid in extracts of the cerebellum were freeze-dried for assay of cGMP with a commercial RIA kit (NEN). Protein determinations (Lowery) and statistics (Dunett's t-test) were performed as described previously [P. L. Wcod et al., Neurochem., 19, 975–982 (1980)]. Groups consisted of 7-10 mice. Results are reported in Table V.

TABLE V

| Test Compound. | Cerebellar cGMP (pmol/mg protein ± SEM) |
|---|---|
| Saline | 3.8 ± 0.43 |
| D-Serine (100 μg) | 17.5 ± 2.4 |
| Compound No. 6 (5 μg) | 3.5 ± 0.55 |
| D-Serine (100 μg) + Compound No. 6 (5 μg) | 5.8 ± 0.96 |

Also embraced within this invention is a class of pharmaceutical compositions comprising one or more compounds of Formula I in association with one or more nontoxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended Therapeutically effective doses of the compounds of the present invention required to prevent or arrest the progress of the medical condition are readily ascertained by one of ordinary skill in the art. The compounds and composition may, for example, be administered intravascularly, intrapertioneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a therapeutically-effective amount of the active ingredient. Examples of such dosage units are tablets or capsules. A suitable daily dose for a mammal may vary widely depending on the condition of the patient, body weight and other factors.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A pharmaceutical composition comprising a therapeutically-effective amount of an antineurotoxic compound and a pharmaceutically-acceptable carrier or diluent, wherein said antineurotoxic compound is selected from compounds of the formula

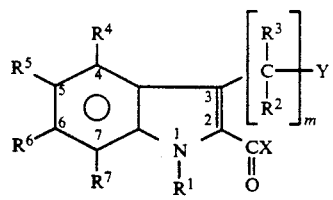

wherein $R^1$ is selected from hydrido, alkyl and aralkyl; wherein each of $R^2$ through $R^7$ is independently selected from hydrido, halo, hydroxy, alkyl, haloalkyl, alkoxy, hydroxyalkyl, cycloalkyl, cycloalkylalkyl, aralkyl, alkoxyalkyl, cyano, alkylthio, sulfinyl, sulfonyl, sulfinylalkyl, sulfonylalkyl, amino, monoalkylamino, dialkylamino, acyl, acyloxy, amido, aryloxy, aralkoxy, aralkoxyalkyl, aryl and

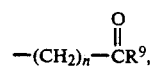

wherein $R^9$ is selected from hydrodo, halo, hydroxy, alkyl, alkoxy, cycloalkyl, cycloalkylalkyl, cycloalkyloxy, aryl, aryloxy, aralkyl, aralkyloxy, amino, monoalkylamino and dialkylamino, wherein n is a number selected from zero through six; wherein X is selected from hydrido, halo, amino, monoalkylamino, dialkylamino and $OR^{10}$ wherein $R^{10}$ is selected from hydrido, alkyl, cycloalkyl, cycloalkylalkyl, aralkyl and aryl; wherein Y is selected from hydrido, alkyl, hydroxy, halo, cycloalkyl, alkoxy and

wherein $R^{11}$ is selected from hydrido, hydroxy, alkyl, alkoxy, cycloalkyl, cycloalkylalkyl, cycloalkyloxy, aryl, aryloxy, aralkyl, aralkyloxy, amino, monoalkylamino and dialkylamino; wherein m is a number selected from zero and one; and wherein any of the foregoing X, Y, $R^1$ through $R^7$, $R^9$, $R^{10}$ and $R^{11}$ substituents having a substitutable position is substituted with a radical selected from alkyl, halo, hydroxy, alkoxy, amino, monoalkylamino, dialkylamino, monoaralkylamino, diaralkylamino, haloalkyl, aralkyl and aryl;

wherein, when any of the foregoing X, Y, $R^1$ through $R^7$ and $R^9$ through $R^{11}$ substituents contains a non-cyclic alkyl portion, or is substituted with a non-cyclic alkyl radical, said non-cyclic alkyl portion or non-cyclic alkyl radical is linear or branched and contains one to about ten carbon atoms; wherein, when any of the foregoing X, Y, $R^2$ through $R^7$ and $R^9$ through $R^{11}$ substituents contains a cyclic alkyl portion, or is substituted with a cyclic alkyl radical, said cyclic alkyl portion or said cyclic alkyl radical contains three to about ten carbon atoms; and wherein, when any of the foregoing X, Y, $R^1$ through $R^7$ and $R^9$ through $R^{11}$ contains an aryl portion or is substituted with an aryl radical, said aryl portion or said aryl radical is selected from phenyl, naphthyl and biphenyl; or a pharmaceutically-acceptable salt or ester thereof.

2. The composition of claim 1 wherein $R^1$ is selected from hydrido, alkyl and aralkyl; wherein each of $R^2$ through $R^7$ is independently selected from hydrido, halo, hydroxy, alkyl, haloalkyl, alkoxy, hydroxyalkyl, cycloalkyl, cycloalkylalkyl, aralkyl, alkoxyalkyl, cyano, alkylthio, amino, monoalkylamino, dialkylamino, acyl, acyloxy, amido, aralkoxyalkyl, aryl and

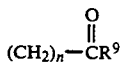

wherein $R^9$ is selected from hydrido, halo, hydroxy, alkyl, alkoxy, cycloalkyl, cycloalkylalkyl, cycloalkyloxy, aryl, aryloxy, aralkyl, aralkyloxy, amino, monoalkylamino and dialkylamino, wherein n is a whole number selected from zero through four; wherein X is selected from halo, amino, monoalkylamino, dialkylamino and $OR^{10}$ wherein $R^{10}$ is selected from hydrido, alkyl, cycloalkyl, cycloalkylalkyl, aralkyl and aryl; wherein Y is selected from hydroxy, halo, alkoxy and

wherein $R^{11}$ is selected from hydrido, halo, hydroxy, alkyl, alkoxy, cycloalkyl, cycloalkylalkyl, cycloalkyloxy, aryl, aryloxy, aralyl, aralkyloxy, amino, monoalkylamino and dialkylamino; wherein m is a number selected from zero and one; and wherein any of the foregoing X, Y, $R^1$ through $R^7$ and $R^9$ through $R^{11}$ substituents having a substitutable position is substituted with a radical selected from alkyl, hydroxy, alkoxy, aralkyl and aryl;
wherein, wherein any of the foregoing X, Y, $R^1$ through $R^7$ and $R^9$ through $R^{11}$ substituents contains a non-cyclic alkyl portion, or is substituted with a non-cyclic alkyl radical, said non-cyclic alkyl portion or non-cyclic alkyl radical is linear or branched and contains one to about ten carbon atoms; wherein, when any of the foregoing X, Y, $R^2$ through $R^7$ and $R^9$ through $R^{11}$ substituents contains a cyclic alkyl portion, or is substituted with a cyclic alkyl radical, said cyclic alkyl portion or said cyclic alkyl radical contains three to about ten carbon atoms; and wherein, when any of the foregoing X, Y, $R^1$ through $R^7$ and $R^9$ through $R^{11}$ contains an aryl portion or is substituted with an aryl radical, said aryl portion or said aryl radical is selected from phenyl, naphthyl and biphenyl; or a pharmaceutically-acceptable salt or ester thereof.

3. The composition of claim 2 wherein $R^1$ is selected form hydrido, alkyl and phenalkyl; wherein each of $R^2$ through $R^3$ si independently selected form hydrido, halo, hydroxy, alkyl, halogalkyl, alkoxy, hydroxyalkyl, phenalkyl, amino, monoalkylamino, dialkylamino and phenyl; wherein each of $R^4$ through $R^7$ is independently selected from hydrido, halo, hydroxy, alkyl, haloalkyl, alkoxy, hydroxyalkyl, phenalkyl, amino, monoalkylamino, dialkylamino, acyloxy, phenyl and

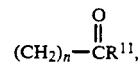

wherein $R^9$ is selected from hydrido, hydroxy, alkyl, alkoxy, phenyl, phenoxy, phenalkyl, phenalkyloxy, amino, monoalkylamino and dialkylamino, wherein n is a whole number selected from zero through four; wherein X is selected from amino, monoalkylamino, dialkylamino and $OR^{10}$ wherein $R^{10}$ is selected from hydrodo, halo, alkyl, phenalkyl and phenyl; wherein Y is selected from hydroxy, halo, alkoxy and

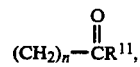

wherein $R^{11}$ is selected from hydrido, hydroxy, alkyl, alkoxy, phenyl, phenoxy, phenalkyl, phenalkyloxy, amino, monoalkylamino and dialkylamino; wherein m is a number selected from zero and one; and wherein any of the foregoing X, Y, $R^1$ through $R^7$ and $R^9$ through $R^{11}$ substituents having a substitutable position is substituted with a radical selected from alkyl, hydroxy, alkoxy, phenalkyl and phenyl;
wherein, when any of the foregoing X, Y, $R^1$ through $R^7$ and $R^9$ through $R^{11}$ substituents contains a non-cyclic alkyl portion, or is substituted with anon-cyclic alkyl radical, said non-cyclic alkyl portion or non-cyclic alkyl radical is linear or branched and contains one to about ten carbon atoms; wherein when any of the foregoing X, Y, $R^2$ through $R^7$ and $R^9$ through $R^{11}$ substituents contains a cyclic alkyl portion, or is substituted with a cyclic alkyl radical, said cyclic alkyl portion or said cyclic alkyl radical contains three to about ten carbon atoms; or a pharmaceutically-acceptable salt or ester thereof.

4. The composition of claim 3 wherein $R^1$ is selected from hydrido and lower alkyl; and wherein each of $R^2$ and $R^3$ is independently selected from hydrido, halo, lower alkyl, benzyl and phenyl; wherein each of $R^4$ through $R^7$ is independently selected from hydrido, halo, hydroxy, lower alkyl, haloalkyl, lower alkoxy, benzyl, phenyl, and

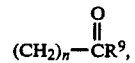

wherein $R^9$ is selected from hydrido, hydroxy, lower alkyl, lower alkoxy, phenyl, phenoxy, benzyl, benzyloxy, amino, monoalkylamino and dialkylamino, wherein n is a whole number selected from zero through two; wherein X is selected from amino, monoalkylamino, dialkylamino and $OR^{10}$ wherein $R^{10}$ is selected from hydrido, lower alkyl, benzyl and phenyl; wherein Y is selected from hydroxy, halo, lower alkoxy and

wherein R[11] is selected from hydrido, hydroxy, lower alkyl, lower alkoxy, phenyl, phenoxy, benzyl, benzyloxy, amino, monoalkylamino and dialkylamino; wherein m is a number selected from zero and one; and wherein any of the foregoing X, Y, R[1] through R[7] and R[9] through R[11] substituents having a substitutable position is substituted with a radical selected from lower alkyl, hydroxy, lower alkoxy, benzyl and phenyl;

wherein, when any of the foregoing X, Y, R[1] through R[7] and R[9] through R[11] substituents contains a non-cyclic alkyl portion, or is substituted with a non-cyclic alkyl radical, said non-cyclic alkyl portion or non-cyclic alkyl radical is linear or branched and contains one to about ten carbon atoms; wherein, when any of the foregoing X, Y, R[2] through R[7] and R[9] through R[11] substituents contains a cyclic alkyl portion, or is substituted with a cyclic alkyl radical, said cyclic alkyl portion or said cyclic alkyl radical contains three to about ten carbon atoms; or a pharmaceutically-acceptable salt or ester thereof.

5. The composition of claim 4 wherein said antineurotoxic compound is of the formula

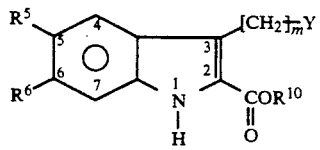

wherein each of R[5] and R[6] is independently selected from hydrido, halo, lower alkyl, haloloweralkyl and lower alkoxy; and wherein R[10] is selected from hydrido, lower alkyl, benzyl and phenyl; wherein Y is selected from hydroxy, lower alkoxy, benzyloxy and

wherein R[11] is selected from hydrido, hydroxy, lower alkyl, lower alkoxy, amino, monoalkylamino, dialkylamino, monophenalkylamino and phenyl; wherein m is one; or a pharmaceutically-acceptable salt thereof.

6. The composition of claim 5 wherein said antineurotoxic compound is of the formula

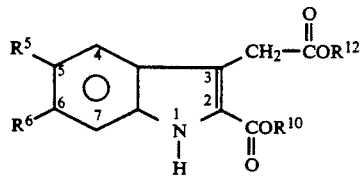

wherein each of R[5] and R[6] is independently selected from hydrido, fluoro, chloro and bromo; wherein R[10] is selected from hydrido and lower alkyl; wherein R[12] is selected from hydrido and lower alkyl; or a pharmaceutically-acceptable salt thereof.

7. The composition of claim 5 wherein said antineurotoxic compound is selected from compounds and their pharmaceutically-acceptable salts of the group consisting of 2-carboxy-3-indolacetic acid;
2-carboxy-1-methyl-3-indoleacetic acid;
2-carboxy-5-chloro-3-indolacetic acid;
5-bromo-2-carboxy-3-indoleacetic acid;
2-carboxy-5-fluoro-3-indoleacetic acid;
ethyl 2-carboxy-6-chloro-3-indoleacetate;
2-carboxy-6-chloro-3-indoleacetamide;
2-carboxy-6-chloro-3-indoleacetic acid 3-ethylamide;
ethyl 6-chloro-3-(2-chloroethyl)-2-indolecarboxylate; and
2-carboxy-6-chloro-3-indoleacetic acid.

8. The composition of claim 7 wherein said antineurotoxic compound is 2-carboxy-6-chloro-3-indoleacetic acid, or a pharmaceutically-acceptable salt thereof.

* * * * *